(12) United States Patent
Okano et al.

(10) Patent No.: US 10,639,822 B2
(45) Date of Patent: May 5, 2020

(54) METHOD OF PRODUCING TRANSDERMAL ABSORPTION SHEET

(71) Applicant: FUJIFILM Corporation, Tokyo (JP)

(72) Inventors: Keio Okano, Kanagawa (JP); Yoshinobu Katagiri, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 390 days.

(21) Appl. No.: 15/643,484

(22) Filed: Jul. 7, 2017

(65) Prior Publication Data
US 2018/0029258 A1  Feb. 1, 2018

(30) Foreign Application Priority Data

Jul. 27, 2016  (JP) ................................ 2016-147085

(51) Int. Cl.
  *B29C 39/02*  (2006.01)
  *A61M 37/00*  (2006.01)
  (Continued)

(52) U.S. Cl.
  CPC .......... *B29C 39/026* (2013.01); *A61K 9/0021* (2013.01); *A61M 37/0015* (2013.01);
  (Continued)

(58) Field of Classification Search
  CPC .. A61M 2037/0053; A61M 2037/0023; A61M 2037/0046; A61M 37/0015;
  (Continued)

(56) References Cited

U.S. PATENT DOCUMENTS 4,876,982 A * 10/1989 Claassen ................. B05C 11/10
                                                                118/406
5,565,033 A * 10/1996 Gaynes ................ B23K 3/0692
                                                                118/210
(Continued)

FOREIGN PATENT DOCUMENTS

JP     2003211049         7/2003
JP     2003211049 A  *  7/2003
(Continued)

OTHER PUBLICATIONS

"Office Action of Japan Counterpart Application," dated Jun. 27, 2019, with English translation thereof, p. 1-p. 13.
(Continued)

*Primary Examiner* — Joseph S Del Sole
*Assistant Examiner* — Jerzi H Moreno Hernandez
(74) *Attorney, Agent, or Firm* — JCIPRNET

(57) ABSTRACT

A method of producing a transdermal absorption sheet including: preparing a mold having needle-like recessed portions including tapered inlet portions; preparing a liquid feeder including an opening portion and a lip land portion; filling the needle-like recessed portions with a solution by feeding the solution to the mold and moving the liquid feeder in a traveling direction while bringing an upstream end of the lip land portion on an upstream side of the liquid feeder in the traveling direction into contact with the mold; and forming needle portions and a sheet portion using a polymer solution. In the filling of the solution, when the upstream end of the lip land portion on the upstream side aligns with an upstream side inlet surface of one of the needle-like recessed portions, the shortest distance from a downstream side inlet surface of the needle-like recessed portion to a surface of the lip land portion on the upstream side is 220 μm or less.

10 Claims, 13 Drawing Sheets

(51) Int. Cl.
*A61K 9/00* (2006.01)
*B29C 39/24* (2006.01)
*B29C 31/04* (2006.01)

(52) U.S. Cl.
CPC ..... *B29C 39/24* (2013.01); *A61M 2037/0046* (2013.01); *A61M 2037/0053* (2013.01); *B29C 31/041* (2013.01); *B29C 31/044* (2013.01)

(58) Field of Classification Search
CPC ............. A61M 2210/04; A61K 9/0021; B29C 39/026; B29C 39/24; B29C 31/041; B29C 31/044
See application file for complete search history.

(56) References Cited

U.S. PATENT DOCUMENTS

2008/0093764 A1* 4/2008 Ito .................... B29C 31/044 264/101ke

| | | | |
|---|---|---|---|
| 2011/0192562 | A1 | 8/2011 | Motoi et al. |
| 2015/0238413 | A1 | 8/2015 | Mochizuki et al. |
| 2017/0057124 | A1 | 3/2017 | Wakamatsu et al. |

FOREIGN PATENT DOCUMENTS

| | | |
|---|---|---|
| JP | 2011078617 | 4/2011 |
| JP | 2015217042 | 12/2015 |
| WO | 2014077242 | 5/2014 |
| WO | 2016143792 | 9/2016 |

OTHER PUBLICATIONS

"Search Report of Europe Counterpart Application", dated Jan. 10, 2018, p. 1-p. 6.

* cited by examiner

METHOD OF PRODUCING TRANSDERMAL ABSORPTION SHEET

CROSS-REFERENCE TO RELATED APPLICATIONS

The present application claims priority under 35 U.S.C. § 119 to Japanese Patent Application No. 2016-147085, filed on Jul. 27, 2016. The above application is hereby expressly incorporated by reference, in its entirety, into the present application.

BACKGROUND OF THE INVENTION

1. Field of the Invention

The present invention relates to a method of producing a transdermal absorption sheet and particularly to a method of producing a transdermal absorption sheet by shape transfer using a mold having needle-like recessed portions formed thereon.

2. Description of the Related Art

As a method for administering a drug or the like through a living body surface, that is, a skin, a mucous membrane, or the like, a drug injection method of using a transdermal absorption sheet on which needle-like protruding portions having a high aspect ratio and containing a drug (hereinafter, also referred to as "microneedles") are formed and inserting the needle-like protruding portions into a skin is used.

In microneedle formation by a needle-like recessed plate using shape transfer, it is necessary to apply a polymer solution to the needle-like recessed plate by any method. For example, JP2011-78617A discloses a method of producing a microneedle sheet by injecting a raw material into a recessed portion of a stamper. WO2014/077242A discloses a method of producing a transdermal absorption sheet including filling needle-like recessed portions of a mold with a solution in a state in which a nozzle is brought into contact with the surface of the mold and moving the nozzle relative to the mold in a state in which the nozzle is brought into contact with the mold to fill the needle-like recessed portions with the solution.

SUMMARY OF THE INVENTION

In the production method disclosed in JP2011-78617A, since the excessive amount of the drug solution applied to the stamper is scraped off by a squeegee, the primary side (on the side on which the squeegee travels) is opened at a so-called free surface, the liquid is not pressurized, and needle-like recessed portions having a high aspect ratio or a water repellent mold cannot be sufficiently filled with the liquid.

In addition, in WO2014/077242A, since the liquid is discharged by pressing a liquid feeding unit in which the height of each lip portion on the primary side and the secondary side is made uniform against the mold and the height of the primary side lip portion and the height of the secondary side lip portion are made uniform, the liquid is jetted to the secondary side and overflows into areas other than the needle-like recessed portions and thus an effective operation cannot be performed.

The present invention is made in consideration of such circumstances and an object thereof is to provide a method of producing a transdermal absorption sheet capable of effectively filling needle-like recessed portions with a liquid.

In order to achieve the above object, according to an aspect of the present invention, there is provided a method of producing a transdermal absorption sheet comprising: an apparatus preparing step of preparing a mold having needle-like recessed portions and having an angle of 120° or more and 160° or less inside the mold, the angle being formed between a flat portion of a surface and an inclined surface of an inlet portion of the needle-like recessed portion, and a liquid feeding apparatus including a slit-shaped opening portion formed at a nozzle tip end portion and a lip land portion; a filling step of filling the needle-like recessed portions with a solution by feeding the solution to the mold from the liquid feeding apparatus and moving the liquid feeding apparatus while, when a travelling direction of the liquid feeding apparatus is set to a primary side and a direction opposite to the travelling direction is set to a secondary side, bringing at least a rear end of the lip land portion on the secondary side into contact with the mold; and a sheet portion forming step of forming needle portions and a sheet portion using a polymer solution, in which in the filling step, when the rear end of the lip land portion on the secondary side of the liquid feeding apparatus matches with a secondary side inlet of the needle-like recessed portion, the shortest length of a distance from a primary side inlet of the needle-like recessed portion to the lip land portion on the secondary side or a wall surface of a secondary side block of the opening portion of the liquid feeding apparatus is 220 µm or less.

According to the aspect of the present invention, in the filling step of filling the needle-like recessed portions with the solution, it is possible to fill the needle-like recessed portions with the solution while scraping off the solution by the rear end of the lip land portion of the secondary side by moving the liquid feeding apparatus while bringing at least the rear end of the lip land portion on the secondary side of the liquid feeding apparatus into contact with the mold. At this time, the solution filling the needle-like recessed portion can be prevented from escaping from the primary side by setting the shortest length of the distance from the primary side inlet of the needle-like recessed portion to the lip land portion of the secondary side or the wall surface of the secondary side block of the opening portion of the liquid feeding apparatus to 220 µm or less when the rear end of the lip land portion of the secondary side of the liquid feeding apparatus matches with the secondary side inlet of the needle-like recessed portion. Accordingly, it is possible to increase the amount of solution filling the needle-like recessed portion.

In addition, the needle-like recessed portion in which the angle formed between the flat portion of the surface of the mold and the inclined surface of the inlet portion of the needle-like recessed portion is 120° or more is easily filled with the solution but the solution is also easily flicked out. According to the present invention, it is possible to increase the amount of solution filling the mold having the needle-like recessed portion having such a shape. In addition, it is also possible to suppress a reduction in the volume of the needle-like recessed portion caused by crushing the mold by the liquid feeding apparatus by setting the angle to 160° or less.

In the aspect of the present invention, it is preferable that the lip land portion on the secondary side of the liquid feeding apparatus is parallel with a straight line connecting the primary side inlet and the secondary side inlet of the needle-like recessed portion.

According to the aspect, since the lip land portion on the secondary side of the liquid feeding apparatus is parallel with the straight line connecting the primary side inlet and the secondary side inlet of the needle-like recessed portion, the solution in the needle-like recessed portion can be suppressed over the entire surface of the lip land portion of the secondary side. Accordingly, it is possible to prevent the solution filling the needle-like recessed portion from escaping and to increase the amount of solution filling the needle-like recessed portion.

In the aspect of the present invention, it is preferable that the lip land portion of the secondary side of the liquid feeding apparatus is inclined to a straight line connecting the primary side inlet and the secondary side inlet of the needle-like recessed portion.

In the aspect of the present invention, it is preferable that the lip land portion of the secondary side of the liquid feeding apparatus is inclined to the straight line connecting the primary side inlet and the secondary side inlet of the needle-like recessed portion in a direction in which the primary side is opened.

According to the aspect, since the lip land portion of the secondary side of the liquid feeding apparatus is inclined to the straight line connecting the primary side inlet and the secondary side inlet of the needle-like recessed portion, a part of the lip land portion of the secondary side is brought into contact with the mold. Accordingly, since the shape of the mold can be stabilized by suppressing deformation of the mold by the lip land portion, it is possible to reduce a variation in filling amount. In addition, since the amount of solution remaining on the surface of the mold can be reduced by making the lip land portion inclined in the direction in which the primary side is opened, it is preferable that the lip land portion is inclined in the direction in which the primary side is opened.

In the aspect of the present invention, it is preferable that a contact distance between the lip land portion of the secondary side of the liquid feeding apparatus and the mold in a travelling direction of the liquid feeding apparatus is 5,000 μm or less.

According to the aspect, since the contact distance between the lip land portion of the secondary side and the mold is 5,000 μm or less, it is possible to prevent the mold from being curled up along the movement of the liquid feeding apparatus.

In the aspect of the present invention, it is preferable that a contact distance between the lip land portion of the secondary side of the liquid feeding apparatus and the mold in a travelling direction of the liquid feeding apparatus is equal to or shorter than the longest distance of the opening portion of the needle-like recessed portion in a moving direction of the liquid feeding apparatus.

According to the aspect, the shape of the needle-like recessed portion can be prevented from being deformed due to crushing of the needle-like recessed portion by the lip land portion of the secondary side when the solution is fed. Accordingly, it is possible to prevent the amount of solution from being reduced after the needle-like recessed portion is filled with the solution and to increase the solution filling amount.

In the aspect of the present invention, it is preferable that the lip land portion of the primary side of the liquid feeding apparatus is not in contact with the mold.

According to the aspect, since the lip land portion of the primary side of the liquid feeding apparatus is not in contact with the mold, damage to the mold can be reduced. In addition, excessive solution can escape from the primary side by preventing the inside of needle-like recessed portion from being pressurized. Accordingly, it is possible to prevent the excessive solution from leaking out from areas other than the primary side. The next needle-like recessed portion in the moving direction of the liquid feeding apparatus can be filled with the solution escaping from the primary side. In the present invention, it is preferable that in the case in which the needle-like recessed portion is not sufficiently filled with the solution, the solution is prevented from escaping from the primary side, and in the case in which the needle-like recessed portion is filled with the solution, the solution is caused to escape from the primary side.

In the aspect of the present invention, it is preferable that the shortest length of a distance between the lip land portion of the primary side of the liquid feeding apparatus and the surface of the mold is 500 μm or less.

According to the aspect, since the shortest length of a distance between the lip land portion of the primary side of the liquid feeding apparatus and the surface of the mold is 500 μm or less, in a state in which the needle-like recessed portion is not filled with the solution, the solution can be prevented from escaping from the primary side. Accordingly, it is possible to increase the amount of solution filling the needle-like recessed portion.

In the aspect of the present invention, it is preferable that the shortest length of the distance between the lip land portion of the primary side of the liquid feeding apparatus and the surface of the mold is 100 μm or more.

According to the aspect, since the shortest length of the distance between the lip land portion of the primary side of the liquid feeding apparatus and the surface of the mold is 100 pin or more, the inside of the needle-like recessed portion can be prevented from being pressurized. Accordingly, it is possible to prevent the solution from leaking out from areas other than the primary side.

In the aspect of the present invention, it is preferable that a surface of the lip land portion of the primary side of the liquid feeding apparatus is formed of a material which is more hydrophobic than the surface of the mold.

According to the aspect, it is possible to prevent the solution from escaping from the primary side by forming the surface of the lip land portion on the primary side of the liquid feeding apparatus using a material which is more hydrophobic than the surface of the mold so as to allow the solution to remain in the needle-like recessed portion.

In the aspect of the present invention, it is preferable that the surface of the lip land portion of the secondary side of the liquid feeding apparatus is formed of a material which is more hydrophilic than the surface of the lip land portion on the primary side.

According to the aspect, since the solution discharged from the slit-shaped opening portion is allowed to remain on the secondary side of the liquid feeding apparatus by forming the surface of the lip land portion of the secondary side of the liquid feeding apparatus using a material which is more hydrophilic than the surface of the lip land portion on the primary side, it is possible to prevent the solution from escaping from the primary side and increase the amount of solution filling the needle-like recessed portion.

In the aspect of the present invention, it is preferable that the opening portion of the liquid feeding apparatus has a notch portion which widens the opening portion on the primary side.

According to the aspect, the solution can be uniformly discharged from the width direction of the opening portion by providing a notch portion on the primary side of the opening portion. Particularly, in the case of using a hydrophobic material for the surface of the lip land portion on the primary side, in the hydrophobic region, there is a concern that the solution is fed to the mold from a portion from which the solution is easily discharged. In this case, a variation in the amount of solution fed to the mold in the width direction of the nozzle occurs and thus a variation in the amount of solution filling the needle-like recessed portion may occur. It is possible to uniformly feed the solution in the width direction by providing the notch portion.

In the aspect of the present invention, it is preferable that a flat portion is provided between the needle-like recessed portions of the mold, and the shortest distance between the needle-like recessed portions is 0.1 mm or more.

According to the aspect, since the solution can be scraped off by the flat portion and the lip land portion on the secondary side of the liquid feeding apparatus by providing the flat portion between the needle-like recessed portions, it is possible to increase the amount of solution filling the needle-like recessed portion.

According to the method of producing a transdermal absorption sheet of the present invention, since the solution filling the needle-like recessed portion can be prevented from escaping from the primary side by defining the length of the opening portion formed by the primary side inlet of the needle-like recessed portion and the lip land portion on the secondary side or the wall surface of the opening portion of the liquid feeding apparatus, it is possible to increase the amount of solution filling the needle-like recessed portion.

DESCRIPTION OF THE PREFERRED EMBODIMENTS

Hereinafter, a method of producing a transdermal absorption sheet of the present invention will be described with reference to the attached drawings. Incidentally, in the specification, numerical values indicated using the expression "to" mean a range including the numerical values indicated before and after the expression "to" as the lower limit and the upper limit.

Transdermal Absorption Sheet

Figure 1:
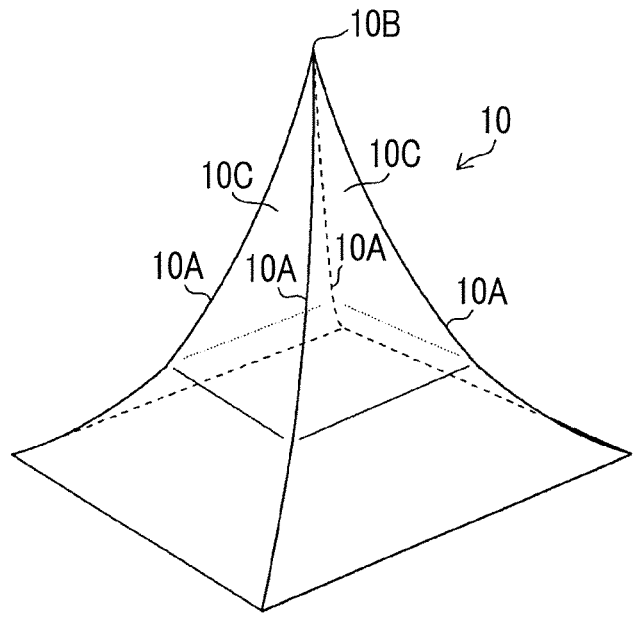
FIG. 1 is a perspective view showing a pyramidal microneedle (needle-like protruding portion) of a transdermal absorption sheet.
Figure 2:
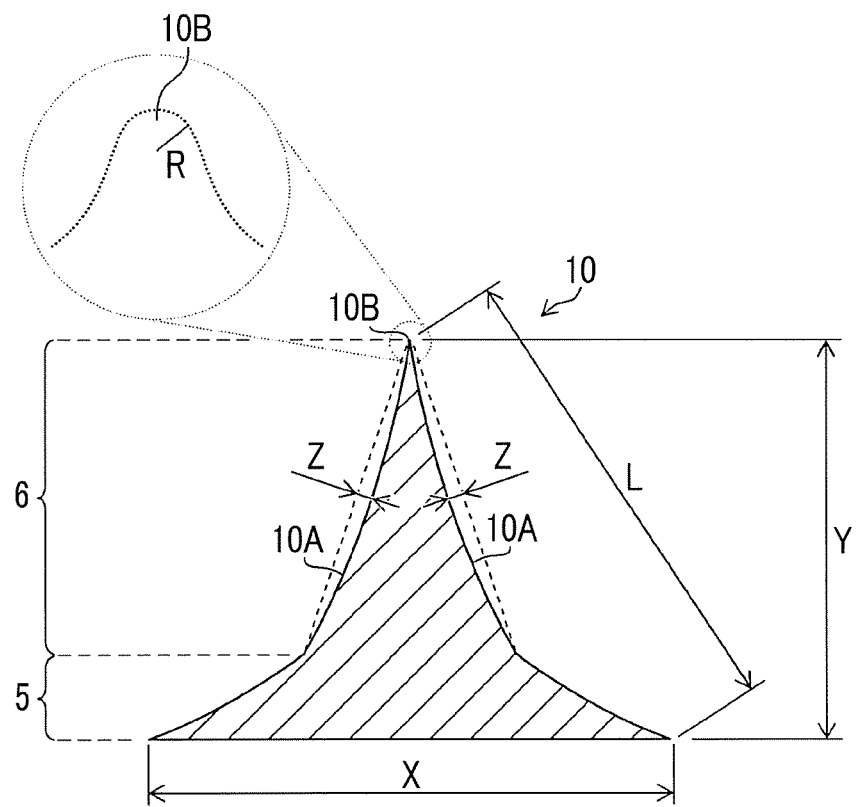
FIG. 2 is a cross-sectional view showing the pyramidal microneedle (needle-like protruding portion) of the transdermal absorption sheet.

The needle-like protruding portions (also referred to as microneedles) on a transdermal absorption sheet produced according to the embodiment will be described. FIG. 1 is a perspective view showing a pyramidal microneedle (needle-like protruding portion) on a transdermal absorption sheet, and FIG. 2 is a cross-sectional view. In the embodiment, example of a quadrangular pyramidal needle-like protruding portion is described, but the present invention is not limited to this shape.

As shown in FIGS. 1 and 2, it is preferable that the microneedle (needle-like protruding portion) 10 formed on the transdermal absorption sheet includes a truncated square pyramid portion 5 and a needle portion 6 formed on the truncated square pyramid portion 5. The needle portion 6 needs to be shaped as follows so that the microneedles 10 can be stuck several hundred μm deep into the surface of the skin: (1) the tip end is sufficiently pointed, and the diameter of the needle penetrating the skin is sufficiently small (the aspect ratio of length/diameter is high), and (2) the microneedle has a sufficient strength (the needle does not bend).

Thus, to meet the requirement in (1), a thin and pointed shape is needed. However, this is opposed to (2), and an excessively thin needle is bent at the tip end or root thereof, whereas an excessively thick needle fails to be stuck into the skin. Thus, as shown in FIG. 1, a ridge line 10A of the needle portion 6 of the microneedle 10 is preferably shaped to be curved toward the inside of the microneedle. The microneedle having such a shape can be made difficult to bend by widening the root while sufficiently sharpening the tip end. Further, the ridge lines 10A and 10A of a quadrangular pyramidal microneedle preferably extend from a quadrangular pyramidal surface 10C between the ridge lines.

The shape of the microneedle 10 is preferably formed such that a side X of a bottom surface is in a range of 0.1 μm or more and 1,000 μm or less, and the height Y is 0.3 μm or more and 3,000 μm or less. More preferably, the side X of the bottom surface is in a range of 10 μm or more and 400 μm or less and the height Y is 30 μm or more and 1,200 μm or less.

When the length of a segment connecting a start point and an end point of the ridge line of the needle portion 6 is represented as L, the maximum depth Z of curve of the ridge line 10A is preferably 0.04×L or more and 0.2×L or less. In addition, the radius of the curvature R of a microneedle tip end 10B, which indicates sharpness of the microneedle 10, is preferably 20 μm or less, and more preferably 15 μm or less.

Figure 3:
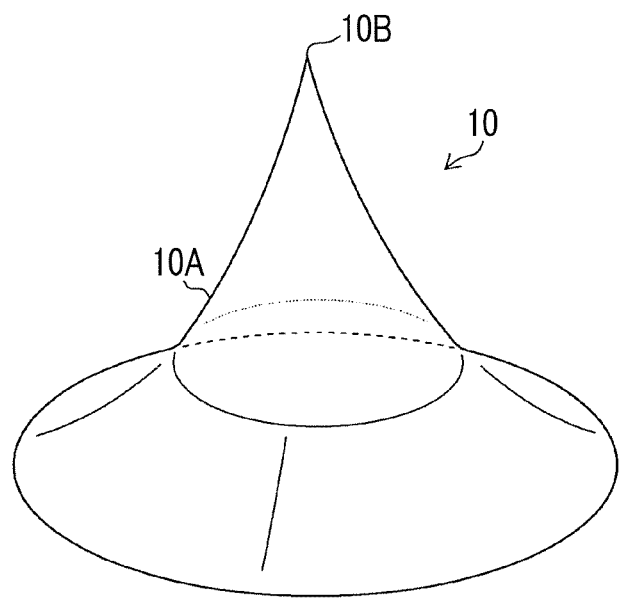
FIG. 3 is a perspective view showing a conical microneedle (needle-like protruding portion) of a transdermal absorption sheet.
Figure 4:
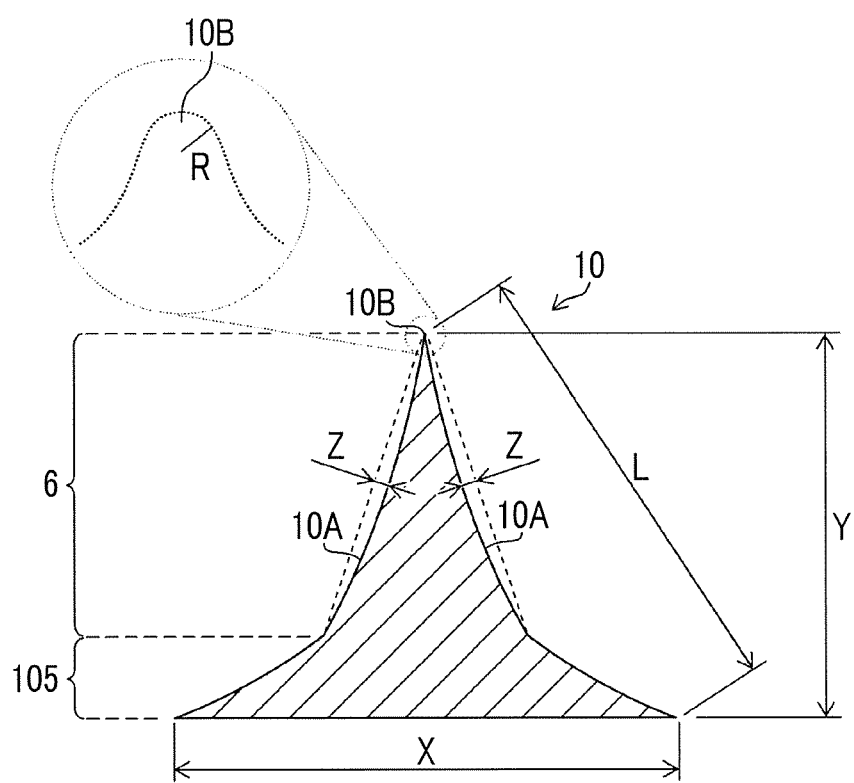
FIG. 4 is a cross-sectional view showing the conical microneedle (needle-like protruding portion) of the transdermal absorption sheet.

FIGS. 1 and 2 show the quadrangular pyramidal microneedle 10. However, a conical microneedle shown in FIGS. 3 and 4 can be adopted. The conical microneedle 10 includes a truncated cone portion 10S and a needle portion 6 formed on the truncated cone portion 10S. In addition, a pyramidal microneedle of another triangular pyramid shape or the like can be adopted. The conical and other pyramidal microneedles are preferably formed to have the same size. In the case of the conical shape, the diameter X of the bottom surface is preferably in a range of 0.1 μm or more and 1,000 μm or less, and more preferably in a range of 50 μm or more and 500 μm or less. In addition, when length of a segment connecting a start point and an end point of the generatrix of the conical surface of the needle portion 6 is represented as L, the maximum depth Z of the curve of the conical surface is preferably 0.04×L or more and 0.2×L or less.

As described above, the transdermal absorption sheet forms a protruding portion array in which the microneedles are arranged in a two-dimensional array. In order to allow the microneedle to be easily stuck into the skin, it is important to sufficiently sharpen the microneedle tip end 10B. The radius of the curvature R of the microneedle tip end 10B is preferably 20 μm or less. In order to form a microneedle 10 having a tip end with a radius of curvature R of 20 μm or less, an important point is whether a solution of a polymer resin can be injected down to the tip end (bottom) of a needle-like recessed portion corresponding to an inverted shape of the protruding portion array to be formed in the mold (form) to allow accurate transfer.

In addition, the transdermal absorption sheet needs to contain a drug, but many drugs are expensive. Thus, it is important to contain a drug in the transdermal absorption sheet such that the drug is concentrated at the portion of each microneedle and to fill the transdermal absorption sheet with the drug with high accuracy in terms of costs.

Method of Producing Transdermal Absorption Sheet

Next, the method of producing the transdermal absorption sheet according to the embodiment of the present invention will be described.

Mold

Figure 5:
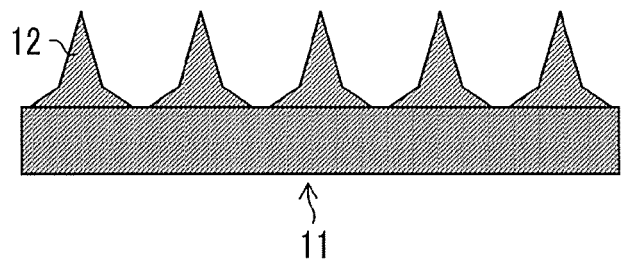
FIG. 5 is a step diagram of a method of producing a mold.
Figure 6:
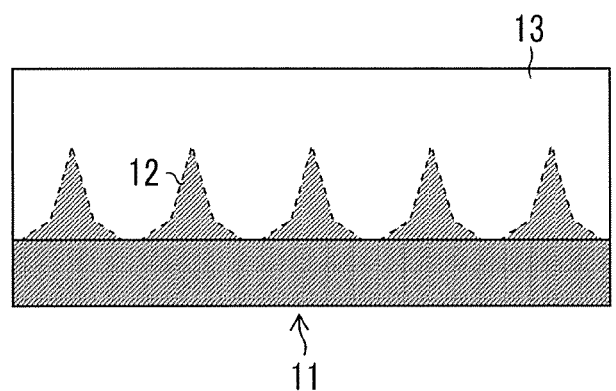
FIG. 6 is a step diagram of the method of producing the mold.
Figure 7:
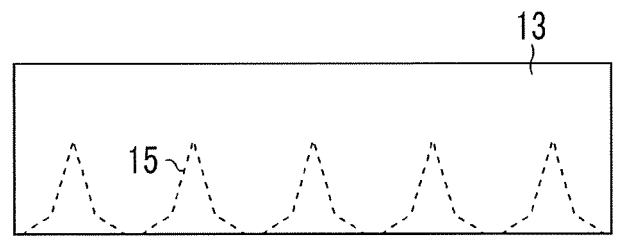
FIG. 7 is a step diagram of the method of producing the mold.

FIGS. 5 to 7 are step diagrams illustrating the production of a mold (form).

As shown in FIG. 5, an original plate which is used to producing a mold for producing the transdermal absorption sheet is first produced.

Two kinds of methods for producing an original plate 11 are available. A first method is a method of applying a photo resist to a Si substrate and then exposing and developing the photo resist. Then, etching such as reactive ion etching (RIE) is performed on the photo resist to produce an array of conical shape portions (needle-like protruding portions) 12 on a surface of the original plate 11. When etching such as RIE is performed so as to form the conical shape portions on the surface of the original plate 11, the conical shapes can be formed by carrying out etching in an oblique direction while the Si substrate is being rotated.

The second method is a method of machining a metal substrate such as Ni using a cutting tool such as a diamond bit to form an array of the shape portions 12 shaped like quadrangular pyramids or the like on the surface of the original plate 11.

Next, the mold is produced. Specifically, as shown in FIG. 6, the mold 13 is produced from the original plate 11. Since the original plate 11 has the shape of cones or pyramids (such as quadrangular pyramids) with pointed tip ends, the following methods are conceived which enables to precisely transfer the shape of the original plate 11 to the mold 13 and then to peel off the mold 13 from the original plate 11, while producing the mold 13 at a low cost.

The first method is a method of pouring, into the original plate 11, a silicone resin containing PDMS (polydimethylsiloxane, for example, SYLGARD 184, manufactured by Dow Corning Toray Co., Ltd.) with a curing agent added thereto, heating and curing the silicone resin at 100° C., and then peeling off the silicone resin from the original plate 11.

The second method is a method of pouring, into the original plate 11, a UV (ultraviolet) curable resin that is curable by irradiation with ultraviolet light, irradiating the UV curable resin with ultraviolet light in a nitrogen atmosphere, and then peeling off the UV curable resin from the original plate 11. The third method is a method of pouring a solution of a plastic resin such as polystyrene or polymethylmethacrylate (PMMA) dissolved into an organic solvent, into the original plate 11 coated with a release agent, volatilizing the organic solvent by drying to cure the plastic resin, and then peeling off the plastic resin from the original plate 11.

Accordingly, the mold 13 in which needle-like recessed portions 15 that are inverted shapes of cones or pyramids on the original plate 11 are arranged in a two-dimensional array is produced. The mold 13 produced as described above is shown in FIG. 7. In addition, the mold 13 can be easily produced any number of times using any of the above-described methods.

Figure 8:
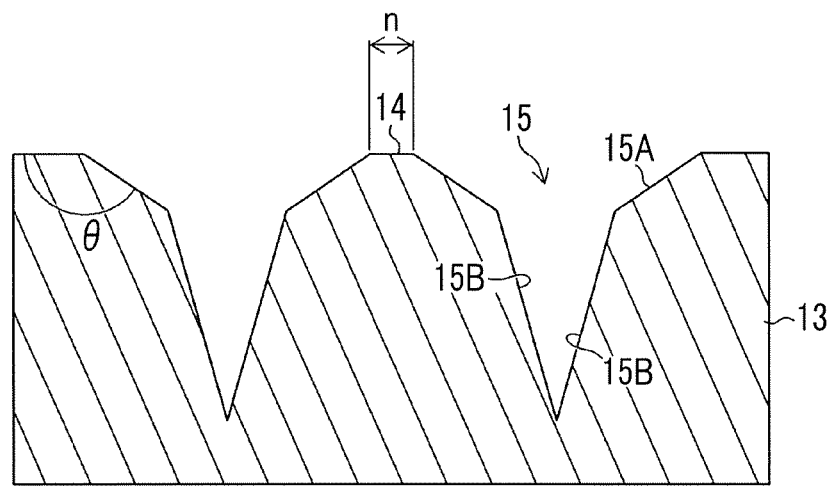
FIG. 8 is a cross-sectional view showing the shape of the needle-like recessed portion of the mold.

FIG. 8 is a cross-sectional view showing an example of the shape of the needle-like recessed portion of the mold. The needle-like recessed portion includes a tapered inlet portion 15A that becomes narrower in a depth direction from the surface of the mold and a tip end recessed portion 15B that is further tapered in the depth direction. Further, an intermediate recessed portion with a constant width in the depth direction may be provided between the inlet portion 15A and the tip end recessed portion 15B or an intermediate recessed portion having a different inclination from the inlet portion 15A and the tip end recessed portion 15B may be provided. One stage intermediate recessed portion or plurality of stages of intermediate recessed portions may be provided.

At the inlet portion 15A of the mold 13, an angle θ, which is an angle formed between the flat portion of the surface of the mold 13 and the inlet portion 15A, is preferably 120° or more and 160° or less inside the mold 13. By setting the angle θ to 120° or more, the solution can be easily introduced into the needle-like recessed portion. In addition, a large number of needle-like recessed portions can be formed in a fixed area by preventing the area of the inlet of the needle-like protruding portion from being increased by setting the angle θ to 160° or less. Thus, the density of needle-like recessed portions in a transdermal absorption sheet to be produced can be increased. Further, when the angle θ is set to be more than 160°, the volume of the needle-like recessed portion is extremely reduced by crushing the mold with the nozzle or the like, and thus the filling amount is not increased and this case is not preferable.

As the material used for the mold 13, an elastic raw material and a metallic raw material can be used. Of these, an elastic raw material is preferable and a raw material with high gas permeability is more preferable. The oxygen permeability, which is representative of the gas permeability, is preferably more than $1\times10^{-12}$ mL/s·m·Pa and more preferably more than $1\times10^{-10}$ mL/s·m·Pa. Setting the gas permeability to be in the above range allows the air present in the needle-like recessed portions 15 in the mold 13 to be driven out from the mold 13 side. Specifically, examples of such materials include materials obtained by melting a silicone resin (for example, SYLGARD 184 or 1310ST), a UV curable resin, or a plastic resin (for example, polystyrene or PMMA (polymethyl methacrylate)), and materials obtained by dissolving any of above resins into a solvent. Among these, a silicone rubber-based raw material can be suitably used because of the durability thereof against transfers by repeated pressurization and the good peelability thereof from the raw material. In addition, in the case of using the transdermal absorption sheet for drugs or the like, safety can be kept. Examples of the metallic raw material include Ni, Cu, Cr, Mo, W, Ir, Tr, Fe, Co, MgO, Ti, Zr, Hf, V, Nb, Ta, α-aluminum oxide, zirconium oxide, stainless steel (STAVAX material), and alloys thereof.

The filling of the mold 13 with the solution is carried out using a nozzle (slit nozzle). In the embodiment, by changing the shapes and materials of the lips of the primary side and the secondary side of the nozzle, the amount of solution filling the needle-like recessed portion can be increased or a variation in the amount of solution filling the needle-like recessed portion can be reduced. The shapes and materials of the lips of the primary side and the secondary side of the nozzle will be described later.

Polymer Solution

The polymer solution that is a solution of the polymer resin used for the material of the transdermal absorption sheet in the embodiment is described.

As the raw material for the resin polymer used for the polymer solution, a biocompatible resin is preferably used. It is preferable to use, as such a resin, sugar such as glucose, maltose, pullulan, dextran, sodium chondroitin sulfate, sodium hyaluronate, hydroxypropyl cellulose, or hydroxyethyl starch, protein such as gelatin, or a biodegradable polymer such as polylactic acid and a lactic acid-glycolic acid copolymer. Among these, sodium chondroitin sulfate, hydroxypropyl cellulose, or dextran can be suitably used. In addition, gelatin-based raw materials have adhesiveness with many base materials and have a high gel strength as materials to be gelated. Thus, in a peeling-off step to be described below, the materials can be brought into tight contact with the base material to allow the polymer sheet to be peeled off from the mold using the base material. Although the concentration varies depending on the material, it is preferable to be such a concentration that 10% to 50% of the resin polymer is contained in the solution. In addition, a solvent to be used for the dissolution may be other than warm water if it has volatility, and methyl ethyl ketone (MEK), alcohol or the like can be used. A drug to be fed to the inside of the human body may concurrently be dissolved into a solution of the polymer resin in accordance with the application.

For the method of preparing the polymer solution, in the case of using a water-soluble polymer (gelatin or the like), the solution can be prepared by dissolving a water-soluble powder into water, and after the dissolution, adding a drug to the solution. In the case in which the material is difficult to dissolve into water, the material may be dissolved by heating. The temperature may be selected appropriately depending on the kind of the polymer material, but the material is preferably heated to a temperature of about 60° C. or lower. Further, in the case in which a thermally melted polymer (maltose or the like) is used, the solution can be prepared by melting the raw material and the drug on heating. The heating temperature is preferably a temperature at which the raw material is melted, and is specifically 150° C.

The viscosity of the solution of the polymer resin is preferably 2,000 Pa·s or less and more preferably 1,000 Pa·s or less. Appropriate adjustment of the viscosity of the solution of the polymer resin facilitates injection of the solution into the needle-like recessed portion of the mold. In addition, the viscosity of the drug-containing solution is preferably 100 Pa·s or less and more preferably 10 Pa·s or less.

Drug

The drug is not limited as long as the drug has the functions as a drug. Particularly, the drug is preferably selected from the group consisting of peptide, protein, nucleic acid, polysaccharide, a vaccine, a medical compound belonging to a water-soluble low-molecular-weight compound, and a cosmetic component. As the water-soluble polymer substance contained in the drug-containing layer, one that does not interact with the drug contained in the layer is preferably used. For example, in the case of using protein as the drug, when a chargeable polymer substance is mixed with the protein, the protein and the polymer substance electrostatically interact with each other to form an aggregate, which is cohered and precipitated. Therefore, in the case in which a chargeable substance is used in the drug, a water-soluble polymer substance with no charge such as hydroxyethyl starch or dextran is preferably used.

Production of Transdermal Absorption Sheet

Figure 9:
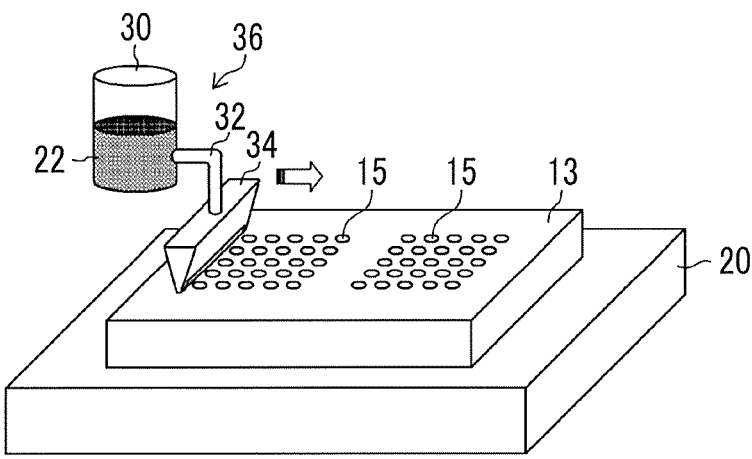
FIG. 9 is a schematic view showing a filling step.
Figure 10:
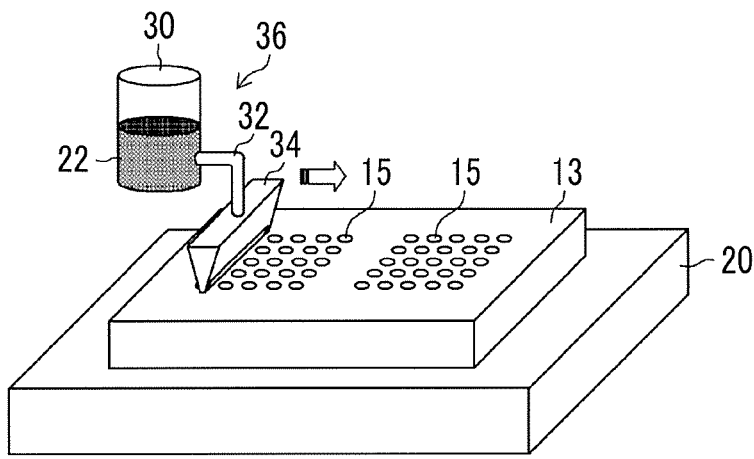
FIG. 10 is a schematic view showing the filling step.
Figure 11:
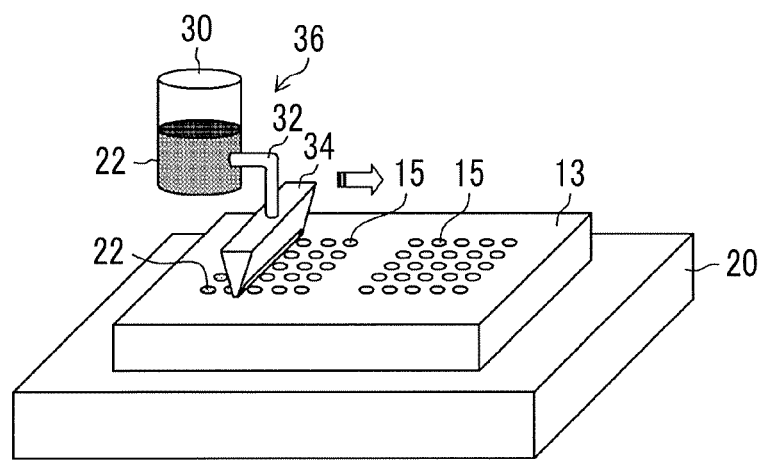
FIG. 11 is a schematic view showing the filling step.

The method of producing the transdermal absorption sheet using the mold 13 produced as described above will be described. FIGS. 9 to 11 are views showing examples of a filling step. As shown in FIG. 9, first, the mold 13 having the two-dimensionally arranged needle-like recessed portions 15 is placed on a base 20. Two sets of a plurality of needle-like recessed portions, each set including 5×5 two-dimensionally arranged needle-like recessed portions, are formed in the mold 13. A liquid feeding apparatus 36 which has a tank 30 housing a drug-containing solution 22, a pipe 32 connected to the tank, and a nozzle 34 connected to a tip end of the pipe 32 is prepared (apparatus preparing step).

Figure 12:
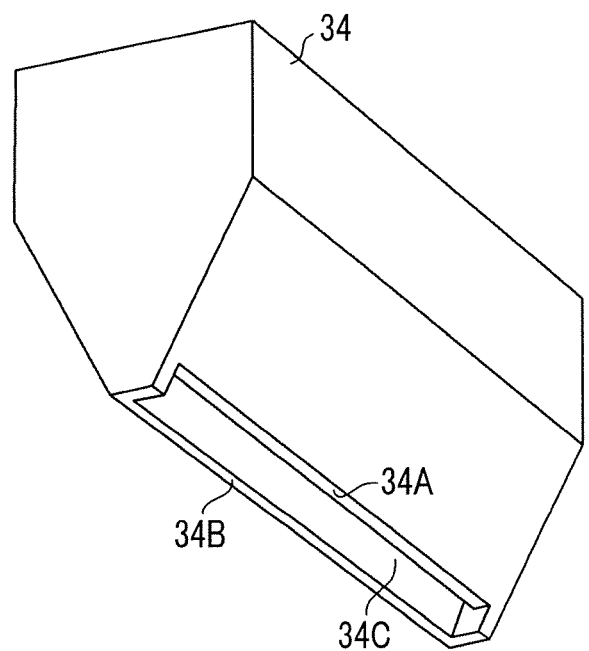
FIG. 12 is a perspective view showing the tip end portion of a nozzle.

FIG. 12 shows a schematic perspective view of the tip end portion of the nozzle. When the travelling direction of the nozzle 34 (the liquid feeding apparatus 36) shown in FIGS. 9 to 11 is set to a primary side and the direction opposite to the travelling direction is set to a secondary side, as shown in FIG. 12, the tip end of the nozzle 34 includes a primary side lip land portion 34A, a secondary side lip land portion 34B, and a slit-shaped opening portion 34C. The slit-shaped opening portion 34C, for example, allows a plurality of needle-like recessed portions 15 constituting one column to be simultaneously filled with the drug-containing solution 22. The size (length and width) of the opening portion 34C is appropriately selected in accordance with the number of needle-like recessed portions 15 to be filled at a time.

An increased length of the opening portion 34C makes it possible to fill an increased number of needle-like recessed portions 15 with the drug-containing solution 22 at a time. Thus, productivity can be improved.

Next, as shown in FIG. 10, the position of the opening portion 34C in the nozzle 34 is adjusted over the needle-like recessed portions 15. The secondary side lip land portion 34B of the nozzle 34 is brought into contact with the surface of the mold 13. The drug-containing solution 22 is fed to the mold 13 from the liquid feeding apparatus 36 to fill the needle-like recessed portions 15 with the drug-containing solution 22 from the opening portion 34C of the nozzle 34. In the embodiment, the plurality of needle-like recessed portions 15 constituting one column is filled with the drug-containing solution 22 at the same time. However, the embodiment is not limited thereto and the needle-like recessed portions 15 can be filled with the solution one by one.

Next, as shown in FIG. 11, while bringing the secondary side lip land portion 34B of the nozzle 34 into contact with the surface of the mold 13, the liquid feeding apparatus 36 and the mold 13 are relatively moved in a direction perpendicular to a length direction of the opening portion 34C, to move the nozzle 34 to the needle-like recessed portions 15 not filled with the drug-containing solution. The position of the opening portion 34C in the nozzle 34 is adjusted over the needle-like recessed portions 15.

Since the nozzle 34 moves while bringing the secondary side lip land portion 34B of the nozzle 34 into contact with the surface of the mold 13, the drug-containing solution 22 remaining on the surface of the mold 13 can be scraped off. Accordingly, the drug-containing solution 22 can be removed in areas of the mold 13 other than the needle-like recessed portions 15.

The 5×5 two-dimensionally arranged needle-like recessed portions 15 are filled with the drug-containing solution 22 by repeating the filling of the drug-containing solution 22 shown in FIG. 10 and the moving of the nozzle 34 in FIG. 11 (filling step). When the 5×5 two-dimensionally arranged needle-like recessed portions 15 are filled with the drug-containing solution 22, the liquid feeding apparatus 36 is moved to adjacent 5×5 two-dimensionally arranged needle-like recessed portions 15 and the filling of the drug-containing solution 22 shown in FIG. 10 and the moving of the nozzle 34 in FIG. 11 are repeated. The adjacent 5×5 two-dimensionally arranged needle-like recessed portions 15 are also filled with the drug-containing solution 22.

The filling of the drug-containing solution 22 and the moving of the nozzle 34 may be in (1) a form in which the drug-containing solution 22 is discharged to the needle-like recessed portions 15 to fill the needle-like recessed portions with the drug-containing solution while the nozzle 34 is being moved, (2) a form in which, while the nozzle 34 is in motion, the nozzle 34 is temporarily stopped over the needle-like recessed portions 15 to fill the needle-like recessed portions 15 with the drug-containing solution 22, and the nozzle 34 is moved again after the filling, or (3) a form in which the drug-containing solution 22 is discharged to just before the needle-like recessed portions 15 (on the secondary side) with respect to the moving direction of the nozzle 34 and the drug-containing solution 22 is scraped off by the secondary side lip land portion 34B of the nozzle 34 to fill the needle-like recessed portions 15 with the drug-containing solution 22. Between the filling of the drug-containing solution 22 and the moving of the nozzle 34, the secondary side lip land portion 34B of the nozzle 34 is in contact with the surface of the mold 13.

When the filling of the needle-like recessed portions 15 with the drug-containing solution 22 is completed, the process proceeds to a sheet portion forming step of forming a polymer sheet with needle-like protruding portions each formed on a surface of the sheet, the polymer sheet including a drug-containing layer constituted of the drug-containing solution 22 and a polymer layer constituted of a non-drug-containing polymer solution. The needle-like protruding portion has an inverted shape of the needle-like recessed portion.

Shape of Tip End of Nozzle

Next, the shape of the tip end of the nozzle 34 used in the filling step will be described. FIGS. 13 to 16 are cross-sectional views showing the shape of the tip end of the nozzle 34 and the shape of the mold 13 used in the method of producing a transdermal absorption sheet of the present invention. As described above, the tip end of the nozzle 34 includes the primary side lip land portion 34A, the secondary side lip land portion 34B, and the slit-shaped opening portion 34C. The fed solution can be scraped off by the secondary side lip land portion 34B by moving the secondary side lip land portion 34B of the nozzle 34 while being in contact with the surface of the mold 13.

Figure 13:
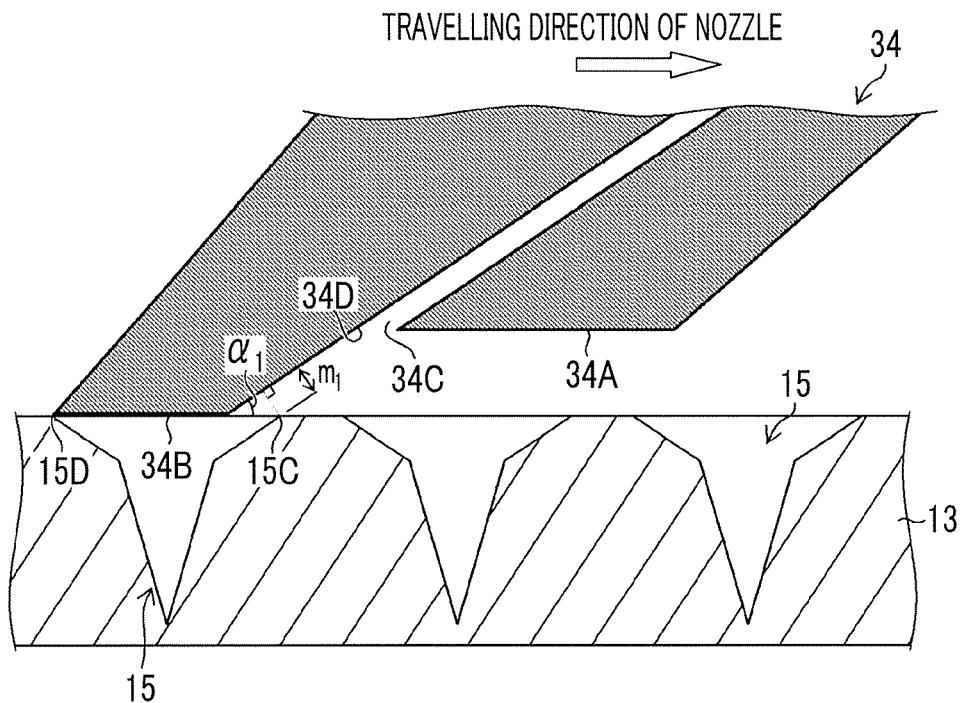
FIG. 13 is a cross-sectional view showing the tip end of the nozzle and the shape of the mold.

A secondary side block for forming the secondary side lip land portion 34B can be formed into a shape such that the secondary side lip land portion 34B shown in FIG. 13 is parallel with the straight line connecting a primary side inlet 15C and a secondary side inlet 15D of the needle-like recessed portion 15. In the shape shown in FIG. 13, the needle-like recessed portion is filled with the solution while the entire surface of the secondary side lip land portion 34B is being brought into contact with the surface of the mold 13. The primary side inlet 15C and the secondary side inlet 15D of the needle-like recessed portion 15 are each a start point of a surface inclined to the surface of the mold 13 at an angle of 160° or less, or, in the case of being bent, a start point in which the straight line connecting the start point and the end point of the bent surface is inclined to the surface of the mold at 160° or less and an inlet portion that is located at the most primary side or secondary side of the needle-like recessed portion.

Figure 14:
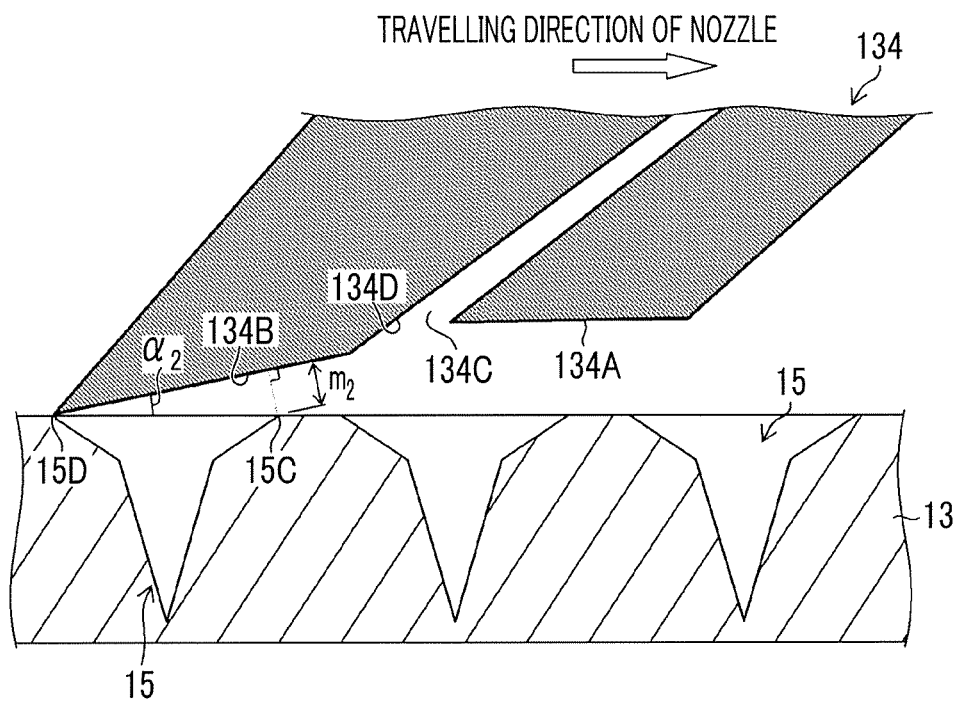
FIG. 14 is a cross-sectional view showing the tip end of another nozzle and the shape of the mold.
Figure 15:
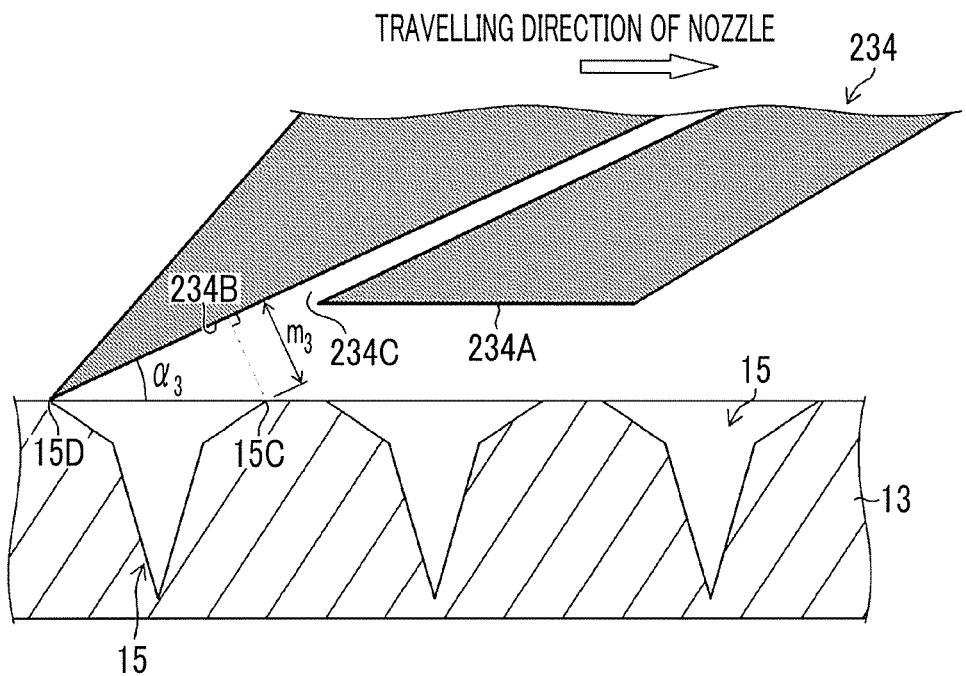
FIG. 15 is a cross-sectional view showing the tip end of yet another nozzle and the shape of the mold.

In addition, as shown in FIGS. 14 and 15, each of secondary side lip land portions 134B and 234B can be formed into a shape such that the secondary side lip land portion is inclined to the straight line connecting the primary side inlet 15C and the secondary side inlet 15D of the needle-like recessed portion 15. In the secondary side lip land portion 134B, as a nozzle 134 shown in FIG. 14, the secondary side lip land portion 134B and a wall surface 134D of an opening portion 134C may be formed on different surfaces and as a nozzle 234 shown in FIG. 15, a wall surface of an opening portion 234C may be formed by extending from the secondary side lip land portion 234B. When the secondary side lip land portion 134B or 234B is made inclined at the time of scraping off the solution by the secondary side lip land portion 134B or 234B, the scraping-off can be carried out while pushing the solution to the needle-like recessed portion 15 side, and thus, the needle-like recessed portion 15 can be easily filled with the solution.

Figure 16:
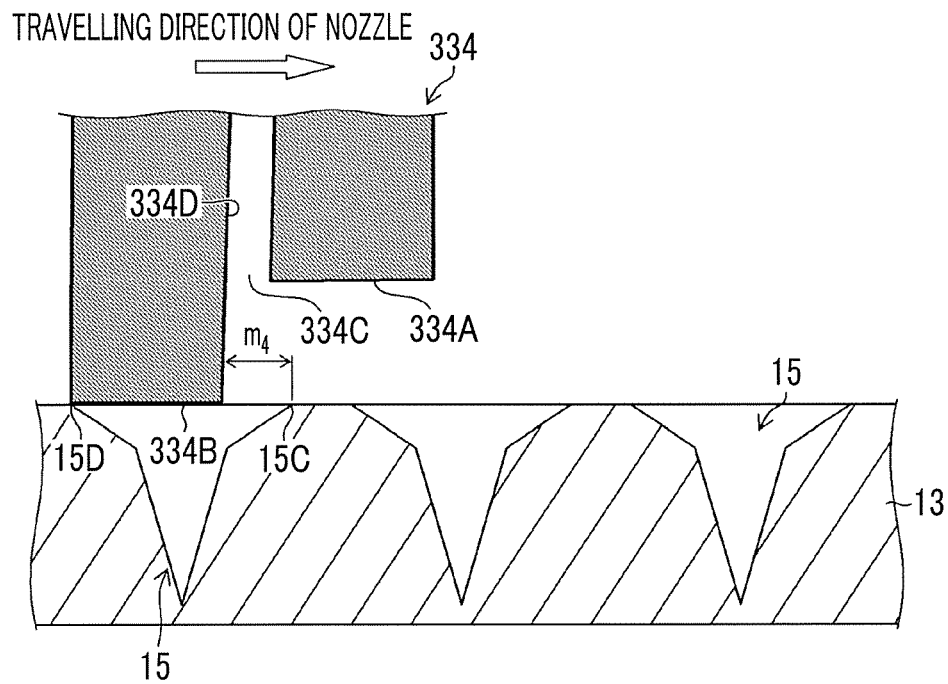
FIG. 16 is a cross-sectional view showing the tip end of yet another nozzle and the shape of the mold.

In FIGS. 13 to 15, the opening portions 34C, 134C, and 234C are inclined to the straight line connecting the primary side inlet 15C and the secondary side inlet 15D of the needle-like recessed portion 15 but as a nozzle 334 shown in FIG. 16, an opening portion 334C can be se to be perpendicular to the straight line connecting the primary side inlet 15C and the secondary side inlet 15D of the needle-like recessed portion 15. In FIG. 16, a secondary side lip land portion 334B is parallel with the straight line connecting the primary side inlet 15C and the secondary side inlet 15D of the needle-like recessed portion 15 but can be inclined to the straight line.

In the embodiment, when the rear end of the secondary side lip land portion 34B of the nozzle 34 matches with the secondary side inlet 15D of the needle-like recessed portion 15, the shortest length of either a distance from the primary side inlet 15C of the needle-like recessed portion 15 to the secondary side lip land portion 34B or a distance from the primary side inlet to a wall surface 34D of the secondary side block of the opening portion 34C (hereinafter, simply referred to as "distance between the secondary side block and the primary side inlet") is 220 μm or less. The shortest length of the distance between the secondary side block and the primary side inlet is preferably 150 μm or less.

The shortest length of either the distance from the inlet on the primary side of the needle-like recessed portion to the secondary side lip land portion or the distance from the primary side inlet to the wall surface of the secondary side block of the opening portion is a length $m_1$ of a perpendicular line drawn to the wall surface 34D of the secondary side block of the opening portion 34C from the primary side inlet 15C of the needle-like recessed portion 15 in the case in which the opening portion 34C is inclined and the length of the secondary side lip land portion 34B is shorter than the diameter of the needle-like recessed portion 15 as shown in FIG. 13.

In the case in which the length of the secondary side lip land portion 134B or 234B is longer than the diameter of the needle-like recessed portion 15 as shown in FIGS. 14 and 15, lengths $m_2$ and $m_3$ of a perpendicular line drawn from the primary side inlet 15C of the needle-like recessed portion 15 to the secondary side lip land portion 134B or 234B is the shortest distance. In the case in which the secondary side lip land portion 334B is parallel with the straight line connecting the primary side inlet 15C of the needle-like recessed portion 15 and the secondary side inlet 15D and the opening portion 334C is perpendicular to the straight line as shown in FIG. 16, a distance $m_4$ from the primary side inlet 15C of the needle-like recessed portion 15 to the vertex of the secondary side lip land portion 334B and the wall surface 334D of the opening portion 334C of the nozzle 334 is the shortest distance. In the case in which the opening portion 334C is perpendicular to the straight line connecting the primary side inlet 15C of the needle-like recessed portion 15, the secondary side inlet 15D and the secondary side lip land portion 334B is inclined to the straight line, and the length of the secondary side lip land portion is shorter than the diameter of the needle-like recessed portion 15, as in FIG. 16, the distance from the primary side inlet to the vertex of the secondary side lip land portion 334B and the wall surface 334D of the opening portion 334C is the shortest distance.

In addition, in the case in which the length of the secondary side lip land portion 34B and 334B of the nozzles 34 and 334 is longer than the diameter of the needle-like recessed portion 15 as shown in FIGS. 13 and 16, the secondary side lip land portion 34B or 334B is brought into contact with the primary side inlet 15C of the needle-like recessed portion 15 and thus the shortest length is 0 μm, which is included in the range of the present invention. However, when the length of the secondary side lip land portion 34B or 334B is longer than the diameter of the needle-like recessed portion, the hole collapses and the amount of solution after filling is decreased. Thus, it is preferable that the length of the secondary side lip land portion is set to be shorter than the diameter of the needle-like recessed portion 15 not to cause the hole to collapse.

As described above, the secondary side block of the nozzle 34 is formed such that in a state in which the inlet on the secondary side of the needle-like recessed portion 15 is closed, the distance between the primary side inlet 15C of the needle-like recessed portion 15 and the secondary side block of the nozzle 34 is 220 μm or less and thus the solution filling the needle-like recessed portion 15 can be prevented from escaping. Accordingly, the amount of solution filling the needle-like recessed portion 15 can be increased.

In the case in which the secondary side block of the nozzle 34 is formed such that the secondary side lip land portion 34B or 334B is parallel with the mold 13 as shown in FIGS. 13 and 16, it is preferable that the length of the secondary side lip land portion 34B or 334B is 5 mm or less. When the length of the secondary side lip land portion 34B or 334B parallel with the mold 13, that is, a contact distance of the secondary side lip land portion 34B or 334B and the mold 13 is 5,000 μm or less, in the filling step, the mold 13 can be prevented from curling up due to the movement of the nozzle 34, and the needle-like recessed portion 15 can be stably filled with the solution.

The primary side lip land portion 34A or 334A of the nozzle 34 may be or may not be brought into contact with the mold 13 but is preferably not brought into contact with the mold. Non-contact between the primary side lip land portion 34A and the mold 13 allows damage to the mold 13 to be reduced. In addition, non-contact between the primary side lip land portion 34A or 334A and the mold allows the solution discharged from the opening portion 34C or 334C to be prevented from being pressurized and allows the solution to be prevented from leaking out from the secondary side.

The upper limit of the distance (clearance) between the primary side lip land portion 34A or 334A and the mold 13 is preferably 500 μm or less. When the upper limit of the distance between the primary side lip land portion 34A or 334A and the mold 13 is set to be in the above range, the solution discharged from the opening portion 34C or 334C is prevented from leaking out from the primary side and the amount of solution filling the needle-like recessed portion 15 can be increased.

In addition, the lower limit of the distance (clearance) between the primary side lip land portion 34A or 334A and the mold 13 is preferably 100 μm or more and more preferably 150 μm or more. When the lower limit of the distance between the primary side lip land portion 34A or 334A and the mold 13 is set to be in the above range, the state inside the needle-like recessed portion 15 becomes a pressurized state and the solution can be prevented from leaking out from the secondary side of the needle-like recessed portion 15 after the secondary side lip land portion 34B, 134B, 234B, or 334B of the nozzle 34 passes over the needle-like recessed portion.

The distance between the primary side lip land portion and the mold refers to the shortest length of the distance between the primary side lip land portion of the nozzle and the mold on the perpendicular line of the straight line connecting the primary side inlet 15C and the secondary side inlet 15D of the needle-like recessed portion 15.

As the material used for the nozzle 34, an elastic raw material and a metallic raw material can be used. For example, TEFLON (registered trademark), stainless steel, tungsten, and the like may be used.

In addition, the primary side block and the secondary side block of the nozzle 34 may be formed of different materials. The surface of the primary side lip land portion 34A is preferably formed of a material which is more hydrophobic than the mold 13. For example, in the case in which the mold 13 is formed of a silicone resin, at least the surface of the primary side lip land portion 34A can be formed of TEFLON. When the surface of the primary side lip land portion 34A is more hydrophobic than the mold 13, the solution filling the needle-like recessed portion 15 of the mold 13 can be prevented from escaping from the primary side and thus the amount of solution filling the needle-like recessed portion 15 can be increased.

The surface of the secondary side lip land portion 34B is preferably formed of a material which is more hydrophilic than the surface of the primary side lip land portion 34A. For example, in the case in which the primary side lip land portion 34A is formed of TEFLON, the secondary side lip land portion can be formed of SUS316 (stainless steel). When the surface of the secondary side lip land portion 34B is made more hydrophilic than the primary side lip land portion 34A, the solution can be allowed to remain in the secondary side lip land portion 34B and the solution can be prevented from escaping from the primary side lip land portion 34A. Thus, amount of solution filling the needle-like recessed portion 15 can be increased.

Figure 17:
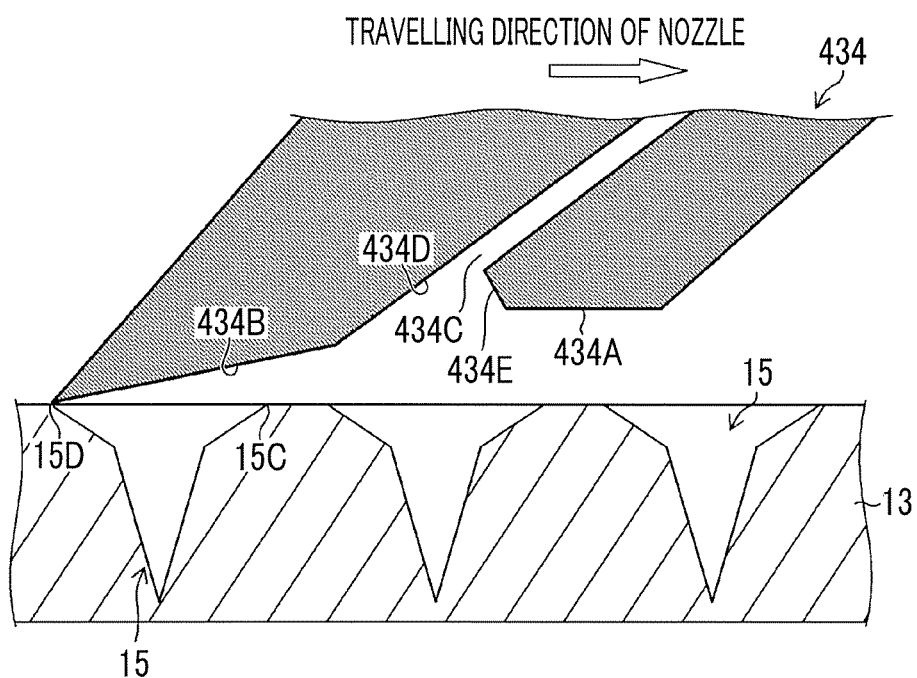
FIG. 17 is a cross-sectional view showing the tip end of yet another nozzle and the shape of the mold.

As the nozzle 434 shown in FIG. 17, the primary side lip land portion 434A of the opening portion 434C is preferably has a notch portion 434E. Particularly, in the case in which the surface of the primary side lip land portion 434A is formed of a hydrophobic material, due to the effect of the hydrophobic material, there is a concern that discharge of the solution may have different distribution in the width direction. When the discharge distribution is different, the amount of solution filling a plurality of needle-like recessed portions 15 arranged in the width direction is different. Provision of the notch portion 434E allows the solution discharged from the opening portion 434C of the nozzle 434 to be uniformed discharged in the width direction.

As shown in FIGS. 13 to 15, the nozzle 34 is preferably inclined in the travelling direction. Inclination of the nozzle 34 in the travelling direction allows the solution to fill the needle-like recessed portion 15 while pushing the solution to the needle-like recessed portion 15 side on the wall surface 34D of the opening portion 34C of the secondary side block or in the secondary side lip land portion 134B or 234B. Thus, the solution remaining on the surface of the mold 13 can be reduced.

Figure 18:
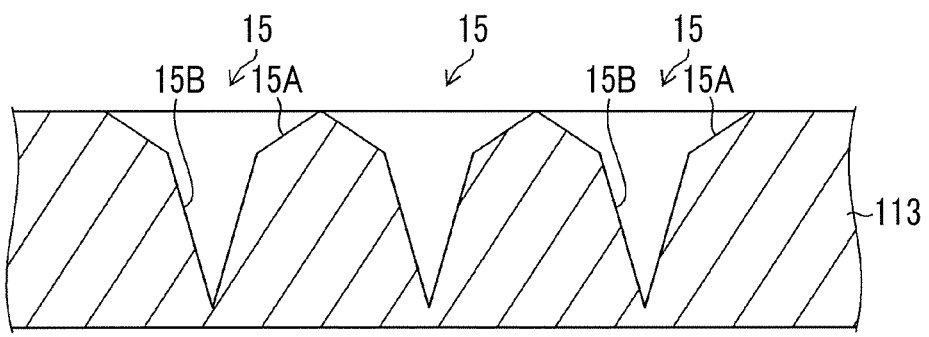
FIG. 18 is a cross-sectional view showing another shape of the mold.

FIG. 18 is a cross-sectional view showing another shape of the mold. As shown in FIG. 18, a mold 113 is different from the mold 13 shown in FIG. 8 in that the needle-like recessed portions 15 are continuously formed. When the needle-like recessed portions 15 are continuously formed, the number of needle-like protruding portions per unit area of a transdermal absorption sheet to be produced can be increased. In addition, as shown in FIG. 8, when the flat portion 14 is provided between the needle-like recessed portions 15, the solution can be split by the flat portion 14 and the secondary side lip land portion 34B and the solution filling amount can be prevented from being reduced by the solution filling the needle-like recessed portion 15 being pulled to adjacent needle-like recessed portions 15. The shortest distance n between the needle-like recessed portions 15 of the flat portion 14 is preferably 0.1 mm or more and more preferably 0.2 mm or more.

Sheet Portion Forming Step (Polymer Sheet Forming Step)

Figure 19:
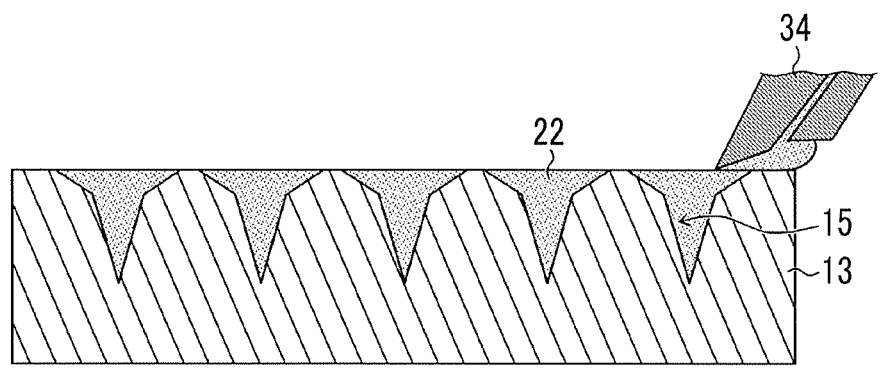
FIG. 19 is a diagram illustrating a sheet portion forming step.
Figure 20:
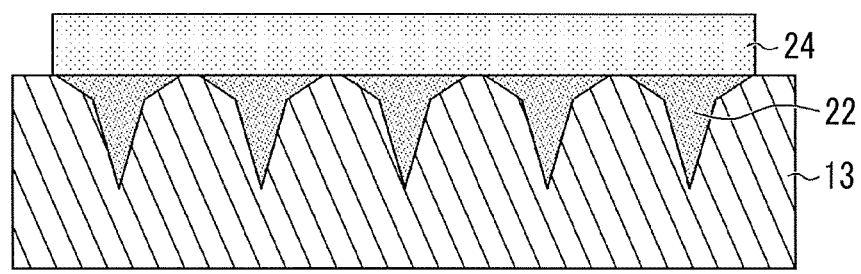
FIG. 20 is a diagram illustrating the sheet portion forming step.

In the sheet portion forming step, several embodiments will be decreased. A first embodiment will be described with reference to FIGS. 19 to 21. For the filling method of the drug-containing solution, as shown in FIGS. 9 to 11, the filling can be performed with contact of the secondary side lip land portion 34B of the nozzle 34 with the mold 13. Next, as shown in FIG. 20, the polymer solution 24 is applied onto the drug-containing solution 22 using a dispenser. In addition to the application using the dispenser, for example, a bar coating method, a spin coating method, and an application using a spray or the like can be adopted.

Figure 21:
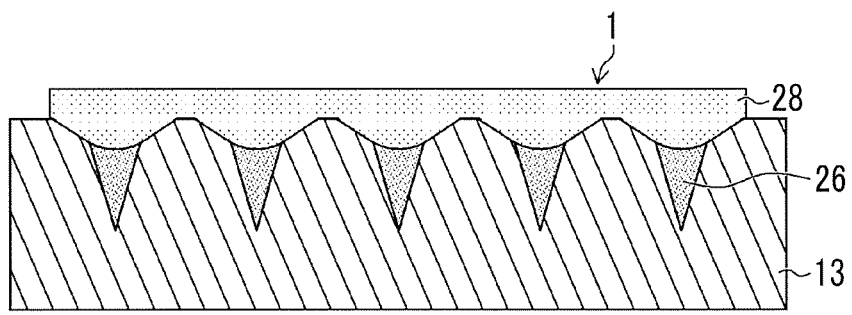
FIG. 21 is a diagram illustrating the sheet portion forming step.

Next, as shown in FIG. 21, the drug-containing solution 22 and the polymer solution 24 are dried and solidified to form a polymer sheet 1 including a drug-containing layer 26 and a polymer layer 28.

Figure 22:
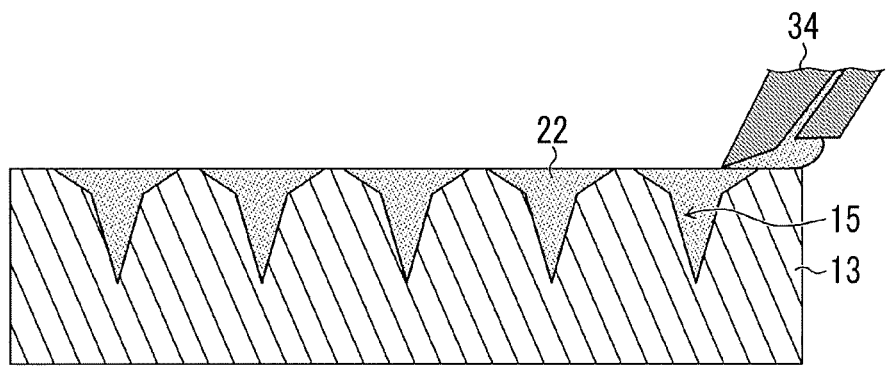
FIG. 22 is a diagram illustrating another sheet portion forming step.
Figure 23:
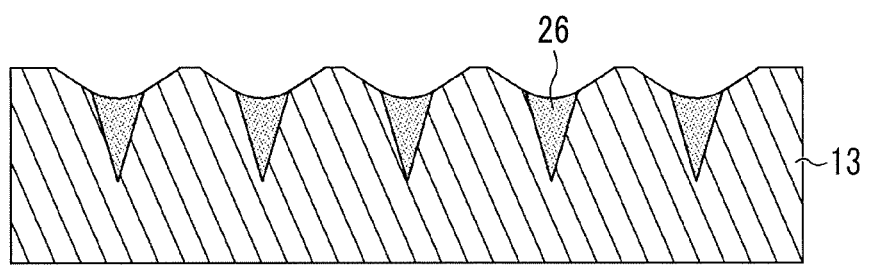
FIG. 23 is a diagram illustrating the other sheet portion forming step.
Figure 24:
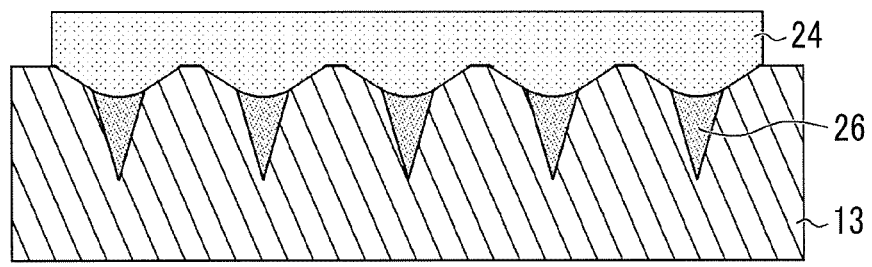
FIG. 24 is a diagram illustrating the other sheet portion forming step.

Next, a second embodiment will be described with reference to FIGS. 22 to 25. As shown in FIG. 22, the needle-like recessed portion 15 of the mold 13 is filled with the drug-containing solution 22. The same filling method as in the first embodiment can be used for the filling method. Next, as shown in FIG. 23, the drug-containing layer 26 is formed in the needle-like recessed portion 15 by drying and solidifying the solutions. Next, as shown in FIG. 24, the polymer solution 24 is applied onto the drug-containing layer 26 using a dispenser. In addition to the application using the dispenser, for example, a bar coating method, a spin coating method, and an application using a spray or the like can be adopted. Since the drug-containing layer 26 is solidified, the drug in the drug-containing layer 26 can be prevented from diffusing into the polymer solution 24.

Figure 25:
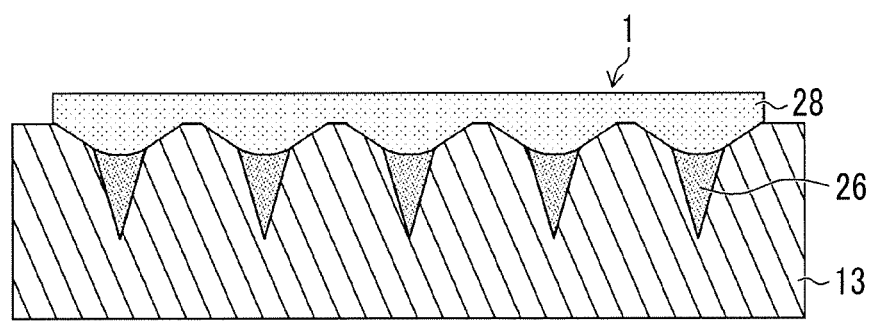
FIG. 25 is a diagram illustrating the other sheet portion forming step.

Next, as shown in FIG. 25, the polymer solution 24 is dried and solidified to form a polymer sheet 1 including the drug-containing layer 26 and the polymer layer 28.

Figure 26:
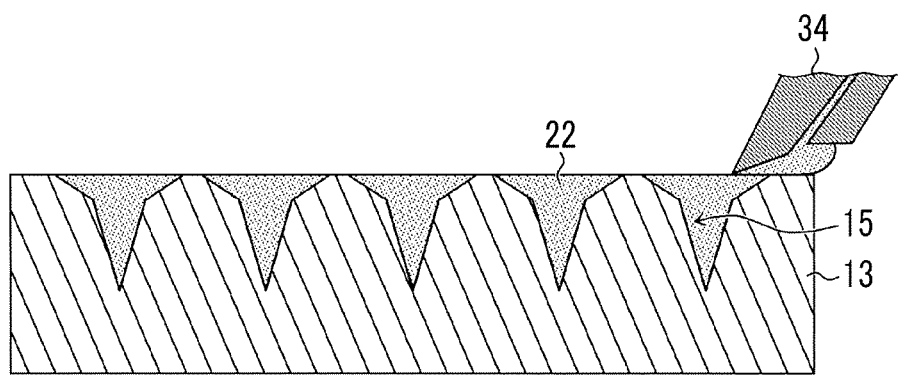
FIG. 26 is a diagram illustrating yet another sheet portion forming step.
Figure 27:
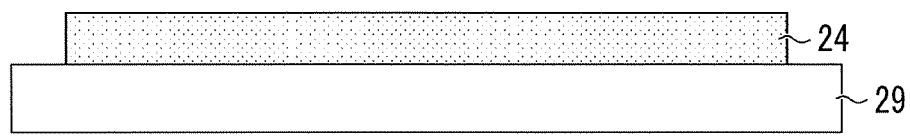
FIG. 27 is a diagram illustrating the other sheet portion forming step.
Figure 28:
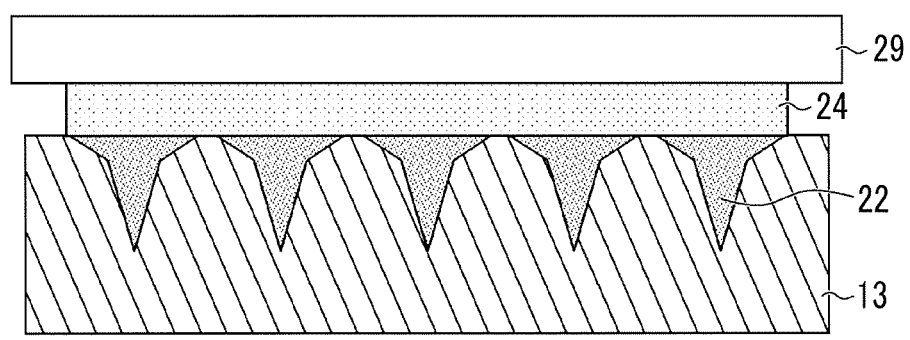
FIG. 28 is a diagram illustrating the other sheet portion forming step.
Figure 29:
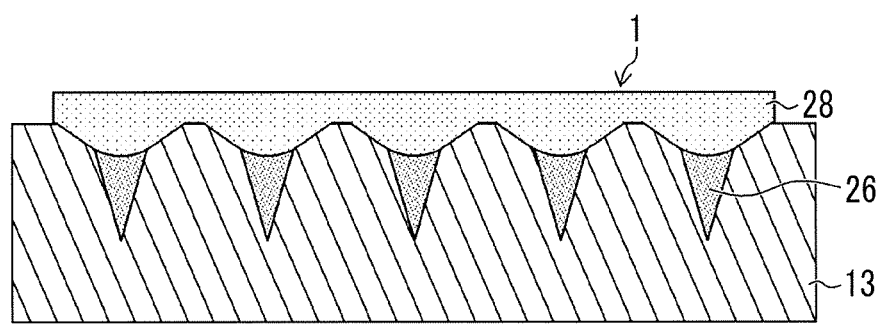
FIG. 29 is a diagram illustrating the other sheet portion forming step.

Next, a third embodiment will be described with reference to FIGS. 26 to 29. As shown in FIG. 26, the needle-like recessed portion 15 of the mold 13 is filled with the drug-containing solution 22. The same filling method as in the first and second embodiments can be used for the filling method. Next, as shown in FIG. 27, the polymer solution 24 is applied onto another support 29. The support 29 is not limited, but for example, polyethylene, polyethylene terephthalate, polycarbonate, polypropylene, an acrylic resin, triacetylcellulose, or the like may be used. Next, as shown in FIG. 28, the polymer solution 24 formed on the support 29 is laid on the mold 13 with the needle-like recessed portion 15 filled with the drug-containing solution 22. Next, as shown in FIG. 29, the drug-containing solution 22 and the polymer solution 24 are dried and solidified to form the polymer sheet 1 including the drug-containing layer 26 and the polymer layer 28.

The polymer sheet 1 having needle-like protruding portions on its surface including the drug-containing layer 26 forming of the drug-containing solution 22 and the polymer layer 28 formed of the polymer solution 24 is formed, and then the process proceeds to a peeling-off step of peeling off the polymer sheet 1 from the mold 13.

Figure 30:
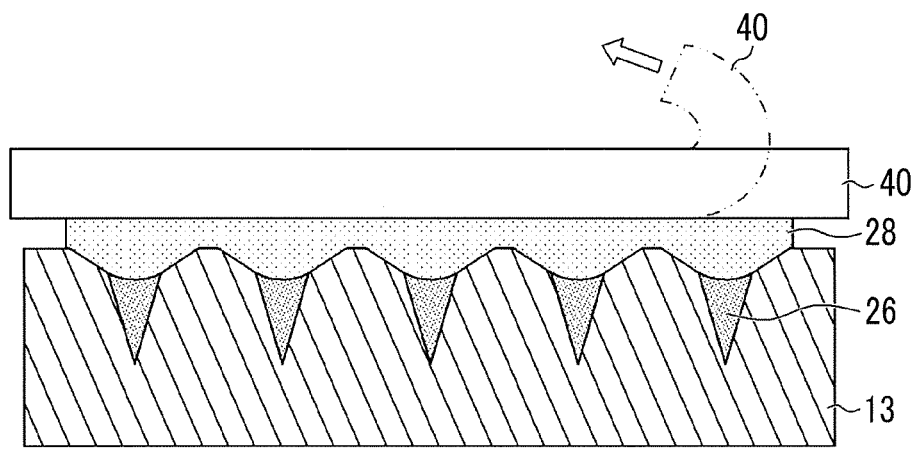
FIG. 30 is a diagram illustrating a peeling-off step.
Figure 31:
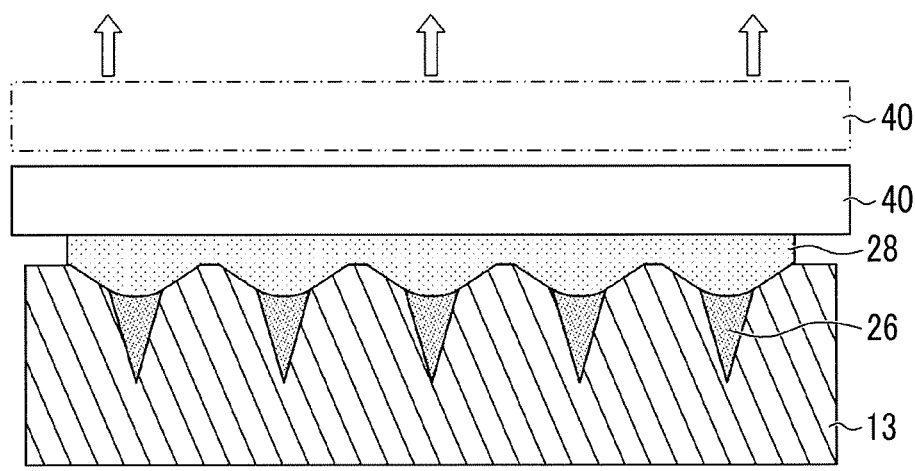
FIG. 31 is a diagram illustrating another peeling-off step.

The method of peeling off the polymer sheet 1 from the mold 13 is not particularly limited. At the time of peeling-off, the needle-like protruding portions are desirably prevented from being bent or broken. Specifically, as shown in FIG. 30, a sheet-like base material 40 on which a pressure sensitive adhesive layer having adhesiveness is forming is attached to the polymer sheet 1, and then the polymer sheet 1 can be peeled off by turning the base material 40 over at the end portion of the polymer sheet. However, this method may cause the needle-like protruding portions to be bent. Therefore, as shown in FIG. 31, the method may be applied in which suckers (not shown) of the polymer sheet 1 are installed on the base material 40 and the base material 40 is then sucked using air and lifted perpendicularly.

Figure 32:
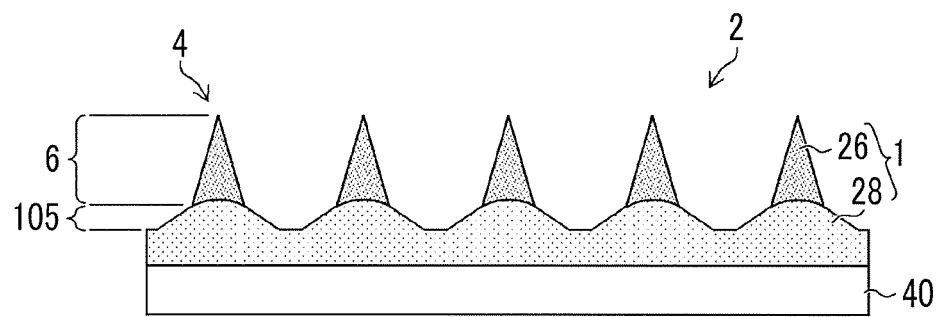
FIG. 32 is a cross-sectional view of a transdermal absorption sheet.

FIG. 32 shows a transdermal absorption sheet 2 includes the polymer sheet 1 peeled off from the mold 13. The transdermal absorption sheet 2 is substantially constituted of the base material 40, the drug-containing layer 26 formed on the base material 40, and the polymer layer 28. Needle-like protruding portions 4 on the transdermal absorption sheet 2 are each constituted of a truncated cone portion 105 and a needle portion 6 on the truncated cone portion 105. The needle portion 6 has a conical or pyramidal needle portion. However, the needle-like protruding portions 4 are not limited to this shape.

EXAMPLES

Hereinafter, the present invention is further specifically described using examples of the present invention. Materials, usages, rates, the contents of treatments, the treatment procedures and the like illustrated in the following examples may be appropriately changed unless the change departs from the spirits of the present invention. Thus, the scope of the present invention should not be interpreted in a limited manner based on the specific examples illustrated below.

Production of Mold

Figure 33:
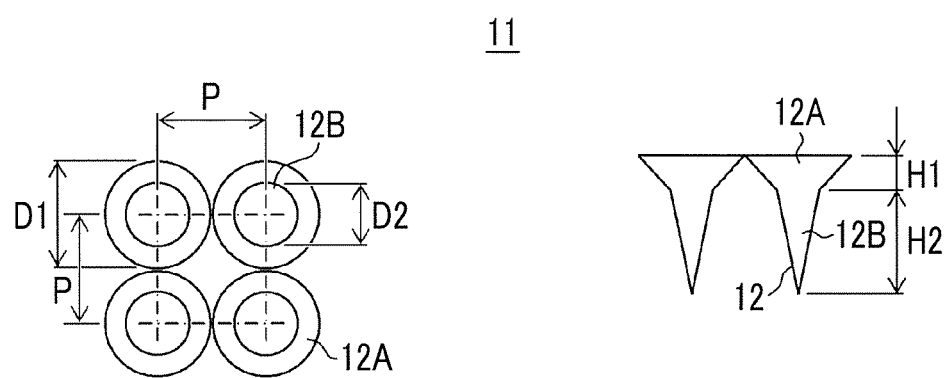
FIG. 33 is a plan view and a side view of an original plate.

As shown in FIG. 33, the original plate 11 was produced by grinding a surface of a smooth Ni plate having one side of 40 mm so as to form shape portions 12 with a needle-like structure that are arranged at a pitch P of 800 µm in a two-dimensional array with 10 columns and 10 rows. Each shape portion 12 with a needle-like structure includes a truncated cone 12A having a bottom surface diameter D1 of 800 µm and a height H1 of 250 µm and a cone 12B formed on the truncated cone 12A and having a diameter D2 of 300 nm and a height H2 of 500 µm.

A film was formed on the original plate 11 having such shape portions 12 with a needle-like structure using various silicone rubbers (SILASTIC-MDX4-4210, manufactured by Dow Corning Toray Co., Ltd.), thermally cured at 120° C. for 5 hours, and peeled-off Thus, an inverted article of the shape portion of a needle-like structure was produced. The inverted article was trimmed so as to leave a planar portion with one side of 30 mm on whose central portion needle-like recessed portions were formed to be two-dimensionally arranged in 10 columns and 10 rows, and the obtained portion was used as a mold. The opening portion side of each of the needle-like recessed portions was the surface of the mold and the needle tip end side was the back surface of the mold. The angle inside the mold of the angle formed between the flat portion of the surface of the produced mold and the inlet portion of the needle-like recessed portion was 135°.

Preparation of Drug-Containing Solution

Hydroxyethyl starch (manufactured by Fresenius Kabi) was dissolved into water to prepare an 8% aqueous solution. 2% by weight of human serum albumin (manufactured by Wako Pure Chemical Industries, Ltd.) and 0.7% by mass of EVANS BLUE dye (manufactured by Wako Pure Chemical Industries, Ltd.) were added to the solution to obtain a solution.

Formation of Drug-Containing Layer

The mold was placed on a horizontal vacuum platform and the back surface of the mold was decompressed with a suction pressure of 50 kPa to the mold to the vacuum platform. A stainless steel nozzle shaped as shown in FIG. 12 was produced and attached to a syringe. The inside of the syringe and the nozzle was filled with 3 mL of the drug-containing solution. The nozzle was adjusted as shown in FIG. 9 in order for the opening to be parallel to the first column formed of a plurality of needle-like recessed portions formed on the surface of the mold. The nozzle was pressed against the mold with a load of 1.76 N at a distance of 2 mm from the first column in a direction opposite to the second column. While the nozzle, kept pressed against the mold, was moved in a direction perpendicular to the length direction of the opening portion at 10 mm/sec, the drug-containing solution was discharged from the nozzle through the opening portion at 0.50 µmL/sec for 10 seconds. The movement of the nozzle was stopped at a distance of 2 mm from the tenth column of the plurality of two-dimensionally arranged needle-like recessed portions in a direction opposite to the ninth column. The nozzle was then separated from the mold.

The mold filled with the drug-containing solution as described above was cut at a position around and 1 mm outside the plurality of two-dimensionally arranged needle-like recessed portions. Drying was performed in a thermohygrostat bath at 30° C. and 40% for 30 minutes to form the drug-containing layer. After the drying, a tape with a low adhesive force was attached to the surface of the mold and then peeled off to remove the drug-containing layer adhering to areas other than the needle-like recessed portions in the mold.

Measurement of the Content of Drug

The mold and the tape with the low adhesive force were each immersed in 1 mL of water in a 5 mL container with a lid. The lid of the container was loosened, and the mold and the tape were pressurized in a pressurized-type degassing unit at 0.5 MPa for 10 minutes. Then, the container was closed and ultrasonic cleaning was carried out for 30 minutes. After it was confirmed that no dye remained on the mold and the tape with the low adhesive force, each of the solutions was measured for absorbance at a wavelength of 620 nm using a microplate absorbance reader (Sunrise Series, manufactured by TECAN). The contents of the drug-containing layer in the needle-like recessed portions and in the areas other than the needle-like recessed portions in the mold were calculated to measure the filling amount.

In the filling of the drug-containing solution, the shape of the nozzle was changed and a filling test was carried out using various nozzles to measure the amount of filling respectively. The filling amount per mold is the total amount of solution filling an array of 10 columns and 10 rows (100 lines). With respect to one kind of nozzle, the filling test was carried out five times and the average filling amount per mold and standard deviation of a variation in filling amount were evaluated.

Experiment 1

For the shape of the nozzle used, a nozzle A shown in FIG. 13, a nozzle B shown in FIG. 14, and a nozzle C shown in FIG. 16, each of which the secondary side lip shape was changed, were prepared to fill the mold with the drug-containing solution. As shown in Table 1, the length of the lip land portion of the nozzle A was changed to 200 to 600 µm. In addition, the angle is $\alpha_1$ shown in FIG. 13 and is an angle formed between the wall surface of the secondary side block of the opening portion of the nozzle and the straight line connecting the primary side inlet and the secondary side inlet of the needle-like recessed portion.

The distance between the lip land portion and the primary side inlet of the needle-like recessed portion of the nozzle B was changed by setting the length of the lip land portion to 1,000 μm to change the angle. The angle is $\alpha_2$ shown in FIG. 14 and is an angle formed between the secondary side lip land portion of the nozzle and the straight line connecting the primary side inlet and the secondary side inlet of the needle-like recessed portion. The distance between the lip land portion and the primary side inlet of the needle-like recessed portion of the nozzle C was changed by changing the length of the lip land portion. Since the diameter of the needle-like recessed portion of the mold is 800 μm, in a nozzle in which the length of the lip land portion is longer than 800 μm, the distance between the lip land portion and the primary side inlet of the needle-like recessed portion is set to 0 μm.

The distance between the primary side lip land portion of the nozzle and the surface of the mold was 500 μm in all the nozzles and the material for the nozzle used was SUS316 for the primary side lip land portion and the secondary side lip land portion.

The results are shown in Table 1.

between the primary side lip land portion of the nozzle and the mold based on Example 2 of Experiment 1. The kind of the nozzle and shape of the nozzle used are the same as those in Example 2. Using the nozzle having the shape of the nozzle A, the length of the lip land portion is set to 600 μm, the angle $\alpha_1$ is set to 45°, and the distance between the secondary side block of the nozzle and the primary side inlet of the needle-like recessed portion is set to 141 μm. The results are shown in Table 2. In addition, the solution leakage from the secondary side was evaluated based on the following criteria.

A . . . No solution leakage occurred
B . . . Solution leakage from the secondary side occurred

TABLE 2

|  | Distance between primary side block of nozzle and mold surface (μm) | Average filling amount [n = five times] (mg) | Solution leakage from secondary side |
| --- | --- | --- | --- |
| Example 2 | 500 | 4.63 | A |
| Example 8 | 300 | 4.71 | A |

TABLE 1

|  | Kind of Nozzle | Shape of Nozzle | | Distance between secondary side block of nozzle and primary side inlet of needle-like recessed portion (μm) | Average filling amount [n = five times] (mg) |
| --- | --- | --- | --- | --- | --- |
|  |  | Length of lip land portion (μm) | Angle (°) |  |  |
| Comparative Example 1 | Nozzle A | 200 | 45 | 353 | 0.23 |
| Comparative Example 2 |  | 200 | 60 | 433 | 0.12 |
| Example 1 |  | 500 | 45 | 212 | 4.21 |
| Comparative Example 3 |  | 500 | 60 | 260 | 1.12 |
| Example 2 |  | 600 | 45 | 141 | 4.63 |
| Example 3 |  | 600 | 60 | 173 | 4.45 |
| Comparative Example 4 | Nozzle B | 1,000 | 60 | 692 | 0.05 |
| Comparative Example 5 |  | 1,000 | 45 | 565 | 0.05 |
| Example 4 |  | 1,000 | 15 | 207 | 4.12 |
| Comparative Example 6 | Nozzle C | 200 | — | 600 | 0.06 |
| Comparative Example 7 |  | 400 | — | 400 | 0.11 |
| Example 5 |  | 600 | — | 200 | 4.16 |
| Example 6 |  | 800 | — | 0 | 3.54 |
| Example 7 |  | 1,000 | — | 0 | 3.31 |

By setting the distance between the secondary side block of the nozzle and the primary side inlet of the needle-like recessed portion to 220 μm or less, the filling amount could be rapidly increased. In addition, by setting to the distance between the secondary side block and the primary side inlet of the needle-like recessed portion even in the nozzle C to 200 μm or less, the solution filling amount could be rapidly increased. In addition, although not shown in the table, the filling was carried out in the nozzle C by changing the length of the lip land portion to 2,000, 5,000, and 8,000 μm. A defect of shifting of the mold at 8,000 μm occurred. Considering the handleability when the filling of the solution is carried out, the length is preferably 5,000 μm or less.

Experiment 2

The solution filling amount and solution leakage from the secondary side were evaluated by changing the distance TABLE 2-continued

|  | Distance between primary side block of nozzle and mold surface (μm) | Average filling amount [n = five times] (mg) | Solution leakage from secondary side |
| --- | --- | --- | --- |
| Example 9 | 100 | 4.86 | A |
| Example 10 | 50 | 4.92 | B |

As shown in Table 2, when the distance between the primary side block and the mold was set to 500 μm or less, the filling amount could be increased. The filling amount could be gradually increased by decreasing the distance between the primary side block and the mold. In addition, at a distance of 50 μm or less, the solution leaked out from the secondary side, thereby resulting in a contamination of the mold surface.

Accordingly, it is considered that the distance between the primary side block and the mold is preferably set to 100 μm or more and 500 μm or less.

Experiment 3

The material for the primary side lip land portion and the secondary side lip land portion of the nozzle was changed based on Example 2 of Experiment 1 to carry out filling. In addition, in Example 10, the nozzle having a notch portion provided on the primary side of the opening portion of the nozzle was used to carry out filling. The results are shown in Table 3.

TABLE 3

| | Material for nozzle | | Average filling amount | Standard deviation |
|---|---|---|---|---|
| | Primary side | Secondary side | [n = five times] (mg) | of filling amount |
| Example 2 | SUS316 | SUS316 | 4.63 | 2.51 |
| Example 11 | TEFLON | TEFLON | 5.11 | 2.30 |
| Example 12 | TEFLON | SUS316 | 5.33 | 1.86 |
| Example 13 | TEFLON Notch portion provided | TEFLON | 5.32 | 1.91 |

As shown in Table 3, in Example 11 in which the material used for the primary side lip land portion and the secondary side lip land portion of the nozzle was TEFLON, the amount of solution filling the nozzle could be increased. In Example 12 in which t the primary side lip land portion was formed of TEFLON and the secondary side block was formed of SUS316, the filling amount could be increased and a variation in filling amount could be also suppressed. This is considered when the primary side lip land portion is formed using TEFLON which is more hydrophobic than the material for the mold and the secondary side lip land portion is formed using SUS316 which is more hydrophilic than the material of the primary side lip land portion, the solution discharged from the nozzle hardly escapes from the primary side and thus the filling amount can be increased.

In addition, in the case in which the material used for the primary side lip land portion and the secondary side lip land portion was TEFLON, in Example 13 in which a notch portion was provided in the primary side block of the opening portion, the solution could be stably discharged. Thus, the solution filling amount could be easily increased and a variation in filling amount can be reduced.

Experiment 4

Experiments 1 to 3 were carried out using the mold in which the needle-like recessed portions are continuously formed as shown in FIGS. 18 and 33, but Experiment 4 was carried out using the mold in which a flat portion was provided between the needle-like recessed portions as shown in FIG. 8 and the length of the flat portion was 50 μm. That is, the mold having a pitch P of 850 μm in FIG. 33 was used. For the nozzle, the nozzle having the shape of Example 2 was used. It could be confirmed that the average value of the filling amounts measured five times in Example 2 was 4.63 mg but an average value of 5.15 mg was obtained by using the mold having a flat portion, thereby increasing the filling amount.

EXPLANATION OF REFERENCES

1: polymer sheet
2: transdermal absorption sheet
4: needle-like protruding portion
5: truncated square pyramid
6: needle portion
10: microneedle
10A: ridge line
10B: microneedle tip end
10C: quadrangular pyramidal surface
11: original plate
12: shape portion
12A: truncated cone
12B: cone
13, 113: mold
14: flat portion
15: needle-like recessed portion
15A: inlet portion
15B: tip end recessed portion
15C: primary side inlet
15D: secondary side inlet
20: base
22: drug-containing solution
24: polymer solution
26: drug-containing layer
28: polymer layer
29: support
30: tank
32: pipe
34, 134, 234, 334, 434 nozzle
34A, 134A, 234A, 334A, 434A: primary side lip land portion
34B, 134B, 234B, 334B, 434B: secondary side lip land portion
34C, 134C, 234C, 334C, 434C: opening portion
34D, 134D, 334D, 434D: wall surface
36: liquid feeding apparatus
40: base material
105: truncated cone portion
434E: notch portion

What is claimed is:

1. A method of producing a transdermal absorption sheet comprising:

preparing a mold having needle-like recessed portions and at least one flat portion located on its upper surface, each of the needle-like recessed portions includes a tapered inlet portion, the at least one flat portion is adjacent to one of the needle-like recessed portions, wherein the at least one flat portion and the tapered inlet portion of the one of the needle-like recessed portions form an angle of 120° or more and 160° or less;

preparing a liquid feeding apparatus including a slit-shaped opening portion formed at a nozzle tip end portion and a lip land portion;

a filling step of filling the needle-like recessed portions with a solution by feeding the solution to the mold from the liquid feeding apparatus and moving the liquid feeding apparatus in a travelling direction, wherein the opening portion of the liquid feeding apparatus divides the lip land portion into two sides, a side at a downstream side with respect to the traveling direction is set as a primary side, and another side at an upstream side with respect to the traveling direction is set as a secondary side, wherein the liquid feeding apparatus is moved such that at least an upstream end of the lip land portion on the secondary side is in contact with the mold; and a sheet portion forming step of forming needle portions and a sheet portion using a polymer solution, wherein in the filling step, when the upstream end of the lip land portion on the secondary side aligns with a side of the tapered inlet portion of the needle-like recessed portion on the secondary side, the shortest distance between a side of the tapered inlet portion of the needle-like recessed portion on the primary side and a surface of the lip land portion of the liquid feeding apparatus on the secondary side nearest to the side of the tapered inlet portion of the needle-like recessed portion on the primary side is 220 µm or less, wherein the lip land portion of the liquid feeding apparatus on the primary side is not in contact with the mold, wherein the shortest distance between the lip land portion of the liquid feeding apparatus on the primary side and the upper surface of the mold is 500 µm or less and 100 µm or more.

2. The method of producing a transdermal absorption sheet according to claim 1,
wherein the lip land portion of the liquid feeding apparatus on the secondary side is parallel with a straight line connecting the side of the tapered inlet portion of the needle-like recessed portion on the primary side and the side of the tapered inlet portion of the needle-like recessed portion on secondary side.

3. The method of producing a transdermal absorption sheet according to claim 1,
wherein the lip land portion of the liquid feeding apparatus on the secondary side is inclined to a straight line connecting the side of the tapered inlet portion of the needle-like recessed portion on the primary side and the side of the tapered inlet portion of the needle-like recessed portion on secondary side.

4. The method of producing a transdermal absorption sheet according to claim 3,
wherein an angle is formed between the lip land portion of the liquid feeding apparatus on the secondary side and the straight line connecting the side of the tapered inlet portion of the needle-like recessed portion on the primary side and the side of the tapered inlet portion of the needle-like recessed portion on the secondary side.

5. The method of producing a transdermal absorption sheet according to claim 2,
wherein a length extending along the traveling direction of the lip land portion of the liquid feeding apparatus on the secondary side that is in contact with the mold is 5,000 µm or less.

6. The method of producing a transdermal absorption sheet according to claim 2,
wherein a length extending along the traveling direction of the lip land portion of the liquid feeding apparatus on the secondary side that is in contact with the mold is equal to or shorter than the longest length of an opening portion of the needle-like recessed portion.

7. The method of producing a transdermal absorption sheet according to claim 1,
wherein a surface of the lip land portion of the liquid feeding apparatus on the primary side is formed of a material which is more hydrophobic than the surface of the mold.

8. The method of producing a transdermal absorption sheet according to claim 1,
wherein the surface of the lip land portion of the liquid feeding apparatus on the secondary side is formed of a material which is more hydrophilic than a surface of lip land portion of the liquid feeding apparatus on the primary side.

9. The method of producing a transdermal absorption sheet according to claim 1,
wherein the lip land portion of the liquid feeding apparatus on the primary side has a notch portion which widens the opening portion of the liquid feeding apparatus on the primary side.

10. The method of producing a transdermal absorption sheet according to claim 1,
wherein the at least one flat portion is provided between adjacent two of the needle-like recessed portions of the mold, and a length of the at least one flat portion is 0.1 mm or more.

* * * * *